United States Patent
Augeri et al.

(10) Patent No.: US 12,215,106 B2
(45) Date of Patent: Feb. 4, 2025

(54) PHARMACEUTICAL COMPOUNDS AND THERAPEUTIC METHODS

(71) Applicant: RUTGERS, THE STATE UNIVERSITY OF NEW JERSEY, New Brunswick, NJ (US)

(72) Inventors: David J. Augeri, New Brunswick, NJ (US); Hatim Sabaawy, New Brunswick, NJ (US); John A. Gilleran, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 664 days.

(21) Appl. No.: 17/297,397

(22) PCT Filed: Nov. 26, 2019

(86) PCT No.: PCT/US2019/063356
§ 371 (c)(1),
(2) Date: May 26, 2021

(87) PCT Pub. No.: WO2020/112845
PCT Pub. Date: Jun. 4, 2020

(65) Prior Publication Data
US 2022/0002296 A1    Jan. 6, 2022

Related U.S. Application Data

(60) Provisional application No. 62/771,956, filed on Nov. 27, 2018.

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01); *C07B 2200/05* (2013.01)

(58) Field of Classification Search
CPC .... C07B 2200/05; A61P 35/00; C07D 471/04
See application file for complete search history.

(56) References Cited

U.S. PATENT DOCUMENTS

| | | |
|---|---|---|
| 8,088,806 B2 | 1/2012 | Zhang et al. |
| 8,680,113 B2 | 3/2014 | Moon et al. |
| 10,875,861 B1 | 12/2020 | Augeri et al. |
| 2002/0041880 A1 | 4/2002 | Defeo-Jones et al. |
| 2011/0190239 A1 | 8/2011 | Moon et al. |
| 2012/0302573 A1 | 11/2012 | Jackson et al. |
| 2016/0046633 A1 | 2/2016 | Alimardanov et al. |

FOREIGN PATENT DOCUMENTS

| | | | |
|---|---|---|---|
| EP | 2306836 B1 | 9/2016 | |
| JP | 2003313176 A | 11/2003 | |
| WO | 2008003511 A1 | 1/2008 | |
| WO | WO-2010002985 A1 * | 1/2010 | ........... A61K 31/425 |

OTHER PUBLICATIONS

Harbeson, S. L., et al., Deuterium in Drug Discovery and Development, Annual Reports in Medicinal Chemistry, vol. 46, Chapter 24, 2011, 404-415. (Year: 2011).*
Uttamsingh, V., et al. Altering Metabolic Profiles of Drugs by Precision Deuteration: Reducing Mechanism-Based Inhibition of CYP2D6 by Paroxetine. J. Pharmacol. Exp. Ther. 354:43-54, Jul. 2015. (Year: 2015).*
Xu, J., et al. The Crucial Roles of Bmi-1 in Cancer: Implications in Pathogenesis, Metastasis, Drug Resistance, and Targeted Therapies. Int. J. Mol. Sci. 2022, 23, 8231. (Year: 2022).*

(Continued)

*Primary Examiner* — Eric Olson
*Assistant Examiner* — Samuel L Galster
(74) *Attorney, Agent, or Firm* — Viksnins Harris Padys Malen LLP

(57) ABSTRACT

The invention provides compounds of formula (16) and (17); and salts thereof, as well as compositions comprising such compounds and salts, complexes comprising such compounds and salts, and methods for treating cancer, inhibiting BMI1 expression, or treating Huntington's disease using such compounds, salts, and complexes. The compounds, salts, and complexes have potency, permeability, and oral bioavailability that make them particularly useful, for example, for the treatment of glioblastoma.

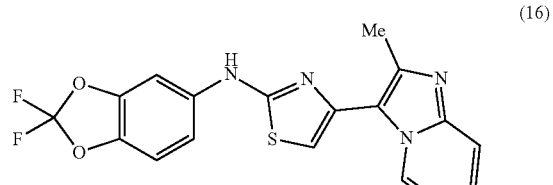

(16)

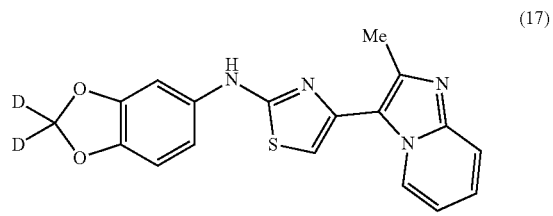

(17)

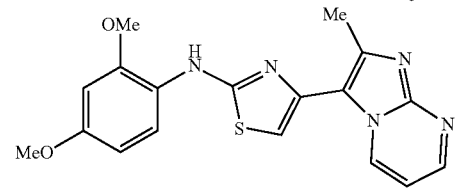

3 Claims, 17 Drawing Sheets

(56) References Cited

OTHER PUBLICATIONS

Bartucci, M , et al., "Synthesis and Characterization of Novel BMI1 Inhibitors Targeting Cellular Self-Renewal in Hepatocellular Carcinoma", Target Oncol 12(4), 449-462 (2017).
Cao, L , et al., "BMI1 as a novel target for drug discovery in cancer", Journal of Cellular Biochemistry 112(10), 2729-2741 (2011).
Chadwick, M , et al., "Development of novel BMI1 inhibitorstargeting glioblastoma stem-like cells [abstract]", Proceedings of the American Association for Cancer Research Annual Meeting 2019; Mar. 29-Apr. 3, 2019; Atlanta, GA. Philadelphia (PA): AACR; Cancer Res 2019;79(13 Suppl): Abstract nr 3073.
Eberle-Singh, J , et al., "Effective Delivery of a Microtubule Polymerization Inhibitor Synergizes with Standard Regimens in Models of Pancreatic Ductal Adenocarcinoma", Clin Cancer Res doi: 10.1158/1078-0432.CCR-18-3281, 14 pages (2019).
Kim, M , et al., "Abstract 5517: PTC596induced Bmi1 hyperphosphorylation via Cdk1/2 activation resulting in tumor stem cell depletion", Proceedings: AACR Annual Meeting, San Diego, CA, Apr. 5-9, 2014.
Nishida, Y , et al., "The novel BMI-1 inhibitor PTC596 downregulates MCL-1 and induces p53-independent mitochondrial apoptosis in acute myeloid leukemia progenitor cells", Blood Cancer Journal 7, e527 (2017).
Patent Cooperation Treaty , International Search Report and Written Opinion for PCT/US2019/063356, 10 pages, dated Jan. 29, 2020.
Zencak, D , et al., "Retinal degeneration depends on Bmi1 function and reactivation of cell cycle proteins", PNAS E593-E601 (2013).

\* cited by examiner

Linear

Semi-Log

Linear

Semi-Log

Figure 17 – TABLE 08

| Matrix | Route | Dose (mg/kg) | Tmax (hr) | #Co/Cmax (ng/mL) | AUClast (hr*ng/mL) | AUCinf (hr*ng/mL) | T1/2 (hr) | CL (mL/min/kg) | Vss (L/kg) | % F |
|---|---|---|---|---|---|---|---|---|---|---|
| Plasma | IV | 2 | - | 389.41 | 237.30 | 257.38 | 0.88 | 129.31 | 7.43 | - |
| | IP | 10 | 0.35 | 421.92 | 1200.61 | 1277.52 | - | - | - | - |
| | PO | 10 | 0.35 | 260.85 | 759.55 | 770.82 | - | - | - | 64 |
| Matrix | Route | Dose (mg/kg) | Tmax (hr) | #Co/Cmax (ng/g) | AUClast (hr*ng/g) | AUCinf (hr*ng/g) | T1/2 (hr) | CL (mL/min/kg) | Vss (L/kg) | % F |
| Brain | IV | 2 | - | 410.86 | 322.21 | 354.04 | 0.93 | 94.15 | 6.02 | - |
| | IP | 10 | 1.00 | 303.10 | 887.52 | NC | - | - | - | - |
| | PO | 10 | 1.00 | 252.91 | 560.86 | NC | - | - | - | - | a – back extrapolated conc. for i.v. group; b – AUC last was considered for calculating oral bioavailability NC – Not calculated due to insufficient data

Figure 18 – TABLE 16

| Matrix | Route | Dose (mg/kg) | Tmax (hr) | aCo/Cmax (ng/mL) | AUClast (hr*ng/mL) | AUCinf (hr*ng/mL) | T1/2 (hr) | CL (mL/min/kg) | Vss (L/kg) | % Fb |
|---|---|---|---|---|---|---|---|---|---|---|
| Plasma | IV | 10 | - | 2180.24 | 722.40 | 725.48 | 0.43 | 229.73 | 4.62 | - |
| | IP | 10 | 0.08 | 712.56 | 346.22 | NC | - | - | - | - |
| | PO | 10 | 0.08 | 175.97 | 149.28 | 147.44 | - | - | - | 20 |

| Matrix | Route | Dose (mg/kg) | Tmax (hr) | aCo/Cmax (ng/g) | AUClast (hr*ng/g) | AUCinf (hr*ng/g) | T1/2 (hr) | CL (mL/min/kg) | Vss (L/kg) | % Fb |
|---|---|---|---|---|---|---|---|---|---|---|
| Brain | IV | 10 | - | 2353.12 | 927.97 | 933.95 | 0.45 | 178.45 | 5.19 | - |
| | IP | 10 | 0.35 | 679.98 | 462.16 | NC | - | - | - | - |
| | PO | 10 | 0.35 | 253.61 | 233.43 | 242.85 | - | - | - | - | a – back extrapolated conc. for i.v. group; b – AUC last was considered for calculating oral bioavailability NC – Not calculated due to insufficient data

Figure 19 – TABLE 25

| Matrix | Route | Dose (mg/kg) | Tmax (hr) | aCo/Cmax (ng/mL) | AUClast (hr*ng/mL) | AUCinf (hr*ng/mL) | T1/2 (hr) | CL (mL/min/kg) | Vss (L/kg) | % Fpo |
|---|---|---|---|---|---|---|---|---|---|---|
| Plasma | IV | 2 | - | 429.68 | 88.73 | 88.20 | 0.31 | NR (377.95) | 4.40 | - |
| | IP | 10 | 0.08 | 469.08 | 673.48 | 785.70 | - | - | - | - |
| | PO | 10 | 0.08 | 306.94 | 482.17 | NR | - | - | - | ~100 (112) |

| Matrix | Route | Dose (mg/kg) | Tmax (hr) | aCo/Cmax (ng/g) | AUClast (hr*ng/g) | AUCinf (hr*ng/g) | T1/2 (hr) | CL (mL/min/kg) | Vss (L/kg) | % Fpo |
|---|---|---|---|---|---|---|---|---|---|---|
| Brain | IV | 2 | - | 44.87 | 97.08 | NC | NC | NC | NC | - |
| | IP | 10 | 0.08 | 288.04 | 160.87 | NR | - | - | - | - |
| | PO | 10 | 0.08 | 67.32 | 111.84 | 204.06 | - | - | - | - | a - back extrapolated conc. for i.v. group; b - AUC last was considered for calculating oral bioavailability
NC – Not calculated due to insufficient data
NR – Not reportable since AUC %Extrap Pred is more than 20%
NR (Clearance): Clearance is not reportable since very high value (377.95 mL/min/kg)

Figure 20 – TABLE 33

| | Compound 100 | Compound 101 | Compound 14 | Compound 15 | Compound 16 | Compound 17 |
|---|---|---|---|---|---|---|
| Potency in patient derived GBM spheres | 5nM | 5nM | 10nM | 1nM | 10nM | 10nM |
| Cellular assays | 5nM Potency in GBM cells | 10nM Potency in GBM cells | Lowered BMI1 levels, lowered STAT1, and lowered pRB | slightly lowered BMI1 levels, lowered STAT1, and lowered pRB | ND | Lowered BMI1 levels, lowered STAT1, lowered pRB, and increased PDL1 (potential immune modulating activity) |
| Caco permeability* | Moderately high | ND | Not permeable/low Mod/High | Not permeable/low High | Moderate | Moderate |
| PPB** | Mod/High | ND | <50% | <50% | High <50% | High <50% |
| Metabolic stability in liver microsomes*** | stable in NAPDH and buffer samples; at 60 min: 26% at 60 min (-NAPDH in Buffer): 40% | ND | ND | | | |
| Pharmacokinetics and brain to plasma levels**** | Tmax (h/s) 0.25 | ND | ND | 1 | 1.5 | 0.48 |
| Oral bioavailability | 4% | ND | ND | 0.9% | 30% | 11% |

*Caco-2 permeability assay to investigate intestinal permeability

**PPB: Plasma Protein Binding Assay (The extent of drug binding to plasma proteins limits the amount of free drug available to act at the target site and may slow metabolism and elimination. Therefore, an assessment of plasma protein binding (PPB) is important in evaluating a drug's pharmacokinetic (PK) properties as well as its efficacy and safety)

***Metabolic stability is defined as the percentage of parent compound lost over time in the presence of a metabolically active test system. For metabolic stability assays, the typical test systems are liver microsomes, liver S9, or hepatocytes (plated or suspended), depending on the goal of the assay.

****A molecule is commonly deemed "brain penetrant" if its brain-to-plasma concentration ratio ($C_b/C_p$) is >0.04 using nonperfused brain tissue, as cerebral blood volume approximates 4% of total brain volume

PHARMACEUTICAL COMPOUNDS AND THERAPEUTIC METHODS

PRIORITY OF INVENTION

This application claims priority to U.S. Provisional Application No. 62/771,956, filed 27 Nov. 2018. The entire content of this provisional application is hereby incorporated herein by reference.

STATEMENT REGARDING FEDERALLY SPONSORED RESEARCH

This invention was made with government support under CA226746 awarded by the National Institutes of Health. The government has certain rights in the invention.

BACKGROUND OF THE INVENTION

Currently there is a need for immunomodulatory agents, agents that modulate one or more cell cycles and target factors associated with cancer stem cells, and for agents with multiple anti-cancer properties.

SUMMARY OF THE INVENTION

The invention provides novel compounds, compositions, and therapeutic methods. The compounds and compositions are useful as immunomodulatory agents, as cell cycle modulators, and as anti-cancer agents. More specifically, one aspect of the present invention provides a compound of formula 14, 15, 16, or 17:

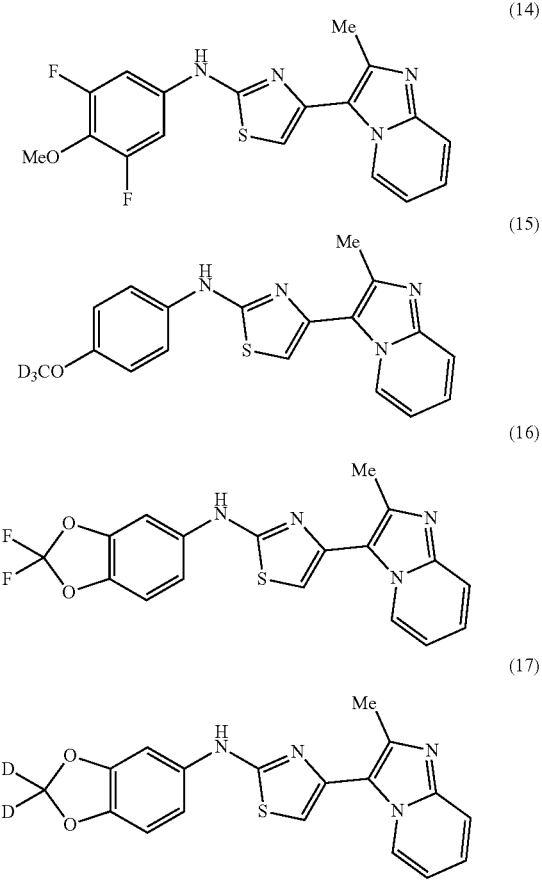

or a salt thereof;

Another aspect of the present invention provides a pharmaceutical composition, comprising, a compound of formula 14, 15, 16, or 17, or a pharmaceutically acceptable salt thereof, and a pharmaceutically acceptable carrier.

Another aspect of the present invention provides a method of inhibiting cancer cell growth, comprising contacting the cancer cell with an effective amount of a compound of formula 14, 15, 16, or 17, or a salt thereof.

Another aspect of the present invention provides a method of treating cancer in an animal (e.g. a human), comprising administering to the animal a compound of formula 14, 15, 16, or 17, or a pharmaceutically acceptable salt thereof.

Another aspect of the present invention provides a compound of formula 14, 15, 16, or 17, or a pharmaceutically acceptable salt thereof for the prophylactic or therapeutic treatment of cancer.

Another aspect of the present invention provides the use of a compound of formula 14, 15, 16, or 17, or a pharmaceutically acceptable salt thereof to prepare a medicament for treating cancer in an animal (e.g. a mammal such as a human).

Another aspect of the present invention provides a method of modulating an immune response in an animal (e.g. a human), comprising administering to the animal a compound of formula 14, 15, 16, or 17, or a pharmaceutically acceptable salt thereof.

Another aspect of the present invention provides a compound of formula 14, 15, 16, or 17, or a pharmaceutically acceptable salt thereof for modulating an immune response.

Another aspect of the present invention provides the use of a compound of formula 14, 15, 16, or 17, or a pharmaceutically acceptable salt thereof to prepare a medicament for modulating an immune response in an animal (e.g. a mammal such as a human).

Another aspect of the present invention provides a method of modulating a cell cycle in an animal (e.g. a human), comprising administering to the animal a compound of formula 14, 15, 16, or 17, or a pharmaceutically acceptable salt thereof.

Another aspect of the present invention provides a compound of formula 14, 15, 16, or 17, or a pharmaceutically acceptable salt thereof for modulating a cell cycle.

Another aspect of the present invention provides the use of a compound of formula 14, 15, 16, or 17, or a pharmaceutically acceptable salt thereof to prepare a medicament for modulating a cell cycle in an animal (e.g. a mammal such as a human).

The invention further includes methods of preparing, methods of separating, and methods of purifying the compounds described herein.

Compounds 16 and 17 possess potency, permeability, and oral bioavailability that make them potential clinical candidates for the treatment of cancers such as, for example, glioblastoma.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

BRIEF DESCRIPTION OF THE FIGURES

FIG. 17. Table 8, shows a summary of mean plasma and brain pharmacokinetic parameters of Compound 15 following a single intravenous (2 mg/kg), intraperitoneal (10 mg/kg) and oral (10 mg/kg) dose administration in male C57BL/6 from Example 12.

FIG. 18. Table 16, shows a summary of mean plasma and brain pharmacokinetic parameters of Compound 16 following a single intravenous (10 mg/kg), intraperitoneal (10 mg/kg) and oral (10 mg/kg) dose administration in male C57BL/6 from Example 13.

FIG. 19. Table 25, shows the mean plasma and brain pharmacokinetic parameters of Compound 17 following a single intravenous (Dose: 2 mg/kg), intraperitoneal (Dose: 10 mg/kg) and oral (Dose: 10 mg/kg) dose administration in male C57BL/6 mice from Example 14.

FIG. 20. Table 33, shows a summary of comparative biological data for Compounds 100, 101, 14, 15, 16, and 17 is provided in Table 34 (FIG. 21).

DESCRIPTION OF THE INVENTION

Figure 1:
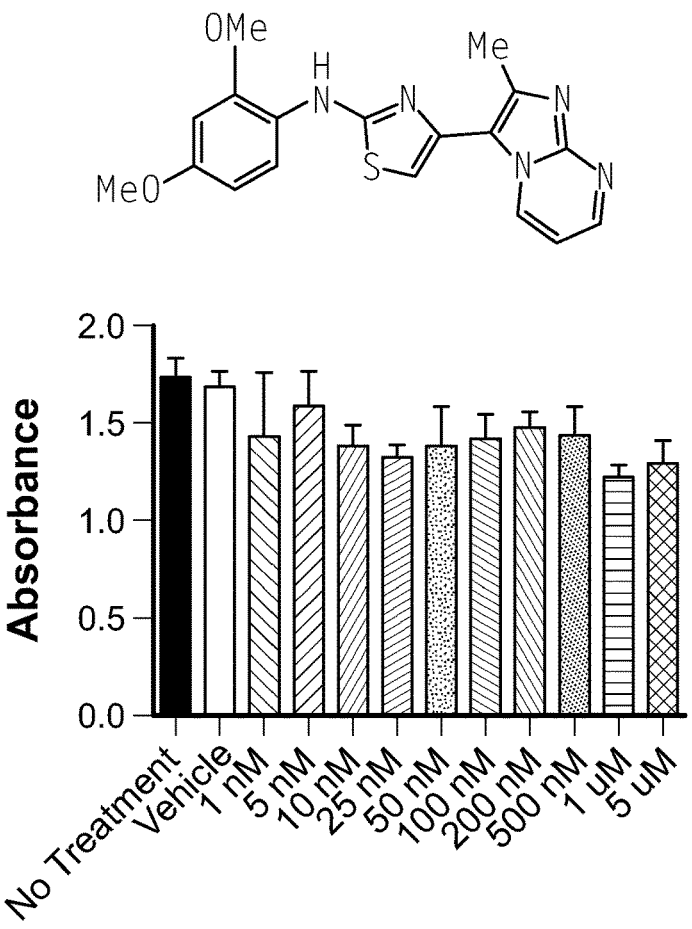
FIG. 1. Shows no antitumor activity of different concentrations of N-(2,4-dimethoxyphenyl)-4-(2-methylimidazo[1, 2-a]pyridin-3-yl)thiazol-2-amine against glioblastoma patient derived spheres, $IC_{80}$>5 mM.
Figure 2:
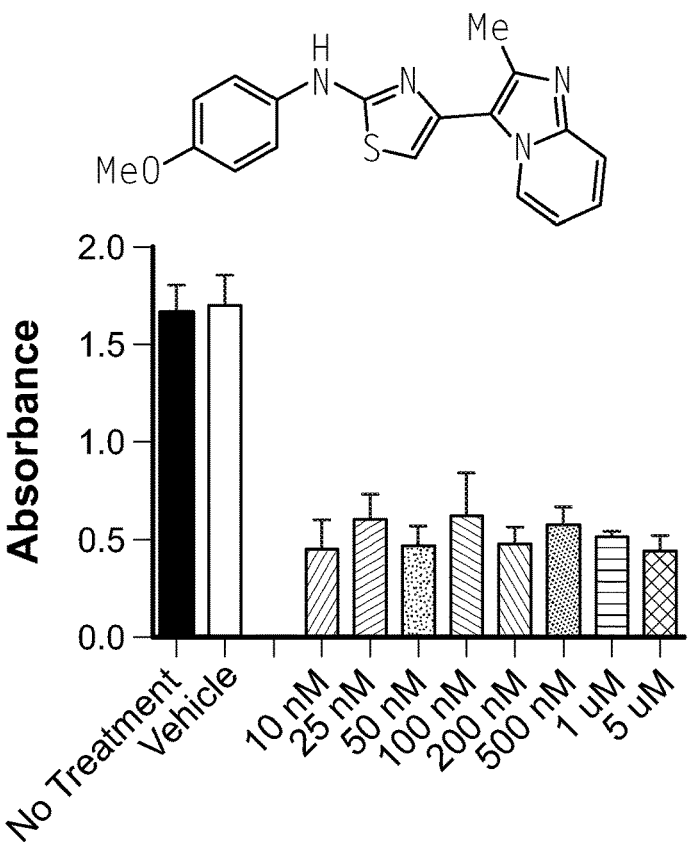
FIG. 2. Shows antitumor activity of different concentrations of N-(4-methoxyphenyl)-4-(2-methylimidazo[1,2-a]pyridin-3-yl)thiazol-2-amine against glioblastoma patient derived spheres, $IC_{50}$=10 nM.
Figure 3:
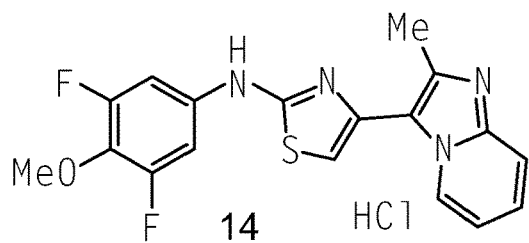
FIG. 3. Shows antitumor activity of different concentrations of N-(3,5-difluoro-4-methoxyphenyl)-4-(2-methylimidazo[1,2-a]pyridin-3-yl)thiazol-2-amine hydrochloride (14) against glioblastoma patient derived spheres, $IC_{50}$=7 nM.
Figure 3:
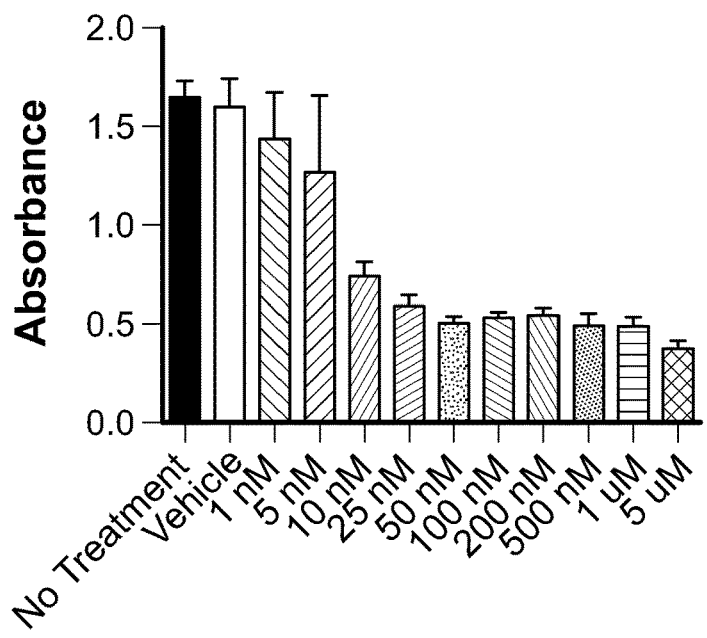
Figure 4:
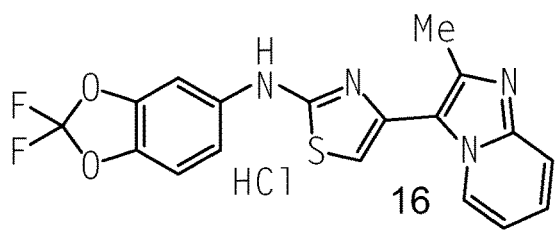
FIG. 4. Shows antitumor activity of different concentrations of N-(2,2-difluorobenzo[d][1,3]dioxol-5-yl)-4-(2-methylimidazo[1,2-a]pyridin-3-yl)thiazol-2-amine hydrochloride (16) against glioblastoma patient derived spheres, $IC_{50}$=200 nM.
Figure 4:
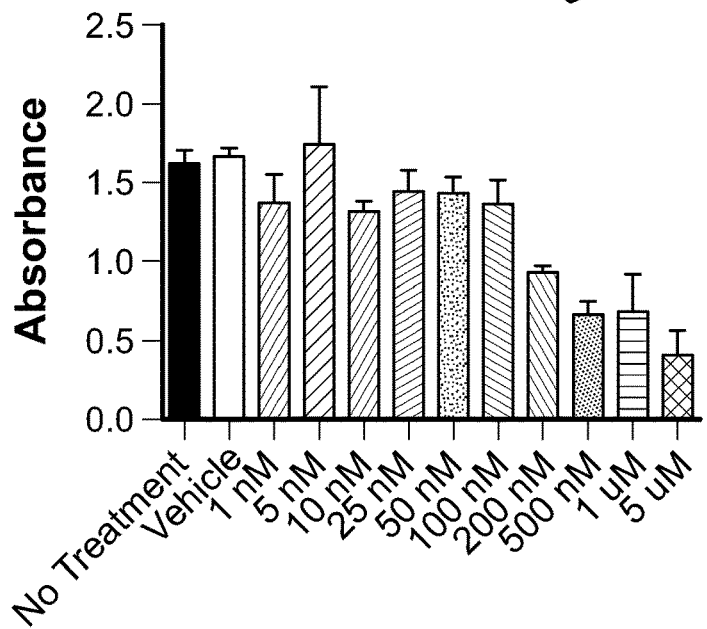
Figure 5:
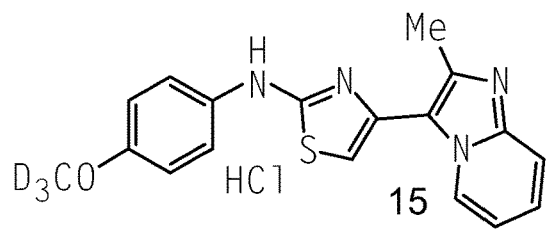
FIG. 5. Shows antitumor activity of different concentrations of N-(4-(methoxy-$d_3$)phenyl)-4-(2-methylimidazo[1,2-a]pyridin-3-yl)thiazol-2-amine hydrochloride (15) against glioblastoma patient derived spheres, $IC_{50}$=7 nM.
Figure 5:
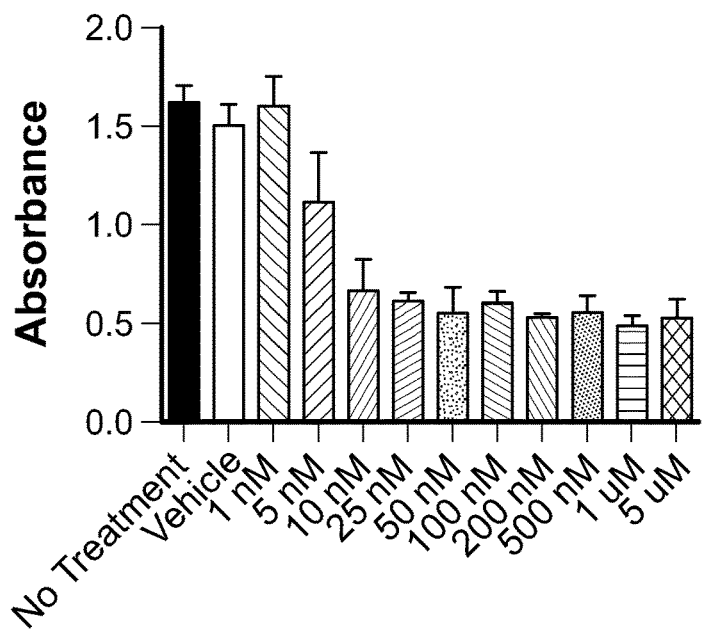
Figure 6:
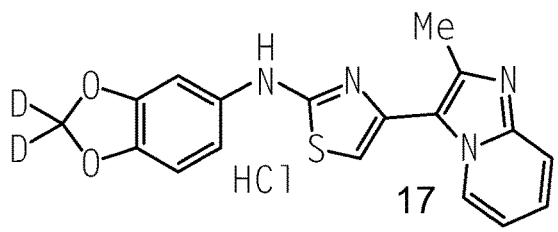
FIG. 6. Shows antitumor activity of different concentrations of N-(benzo[d][1,3]dioxol-5-yl-2,2-$d_2$)-4-(2-methylimidazo[1,2-a]pyridin-3-yl)thiazol-2-amine hydrochloride (17) against glioblastoma patient derived spheres, $IC_{50}$=20 nM.
Figure 6:
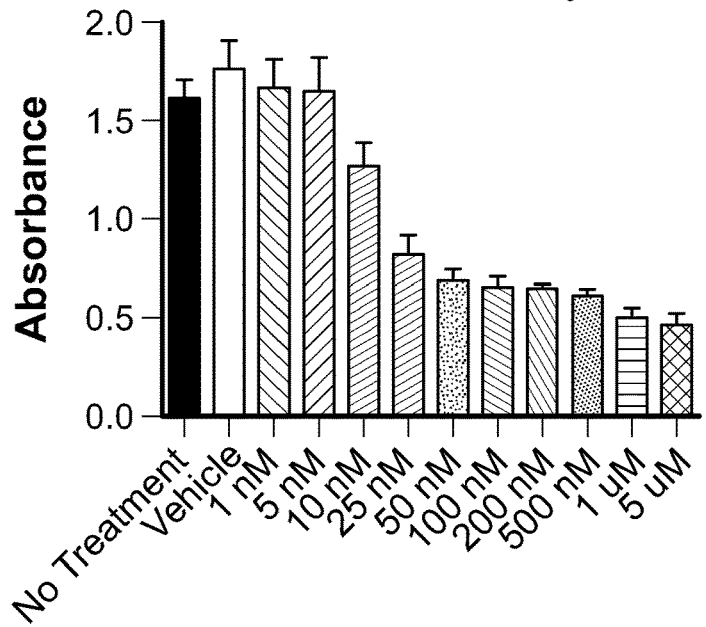

The following definitions are used, unless otherwise described.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention.

The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —OCH$_3$ group may be substituted with —OCD$_3$.

When a compound includes a deuterium in the chemical formula it means the compound is enriched in deuterium at that position above its natural abundance. For example, in one embodiment the abundance of deuterium at that position is substantially greater than the natural abundance of deuterium, which is 0.015%. In another embodiment the abundance of deuterium at that position has a minimum isotopic enrichment factor of at least 3000 (45% deuterium incorporation).

The term "isotopic enrichment factor" as used herein means the ratio between the isotopic abundance and the natural abundance of a specified isotope. In certain embodiments, a compound has an isotopic enrichment factor of at least 3500 (52.5% deuterium incorporation) at a given deuterated atom, at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In some embodiments, 100% deuterium incorporation is achieved.

Deuterium (as well as other isotopes) can be incorporated into a compound using a variety of known reagents and synthetic techniques. For example, deuterium can be incorporated into a compound using LiAlD$_4$. It can also be incorporated into a compound such as through reduction, catalytic hydrogenation or isotopic exchange using appropriate deuterated reagents such as deuterides, D$_2$ and D$_2$O.

The pharmaceutical compositions of the invention can comprise one or more excipients. When used in combination with the pharmaceutical compositions of the invention the term "excipients" refers generally to an additional ingredient that is combined with the compound or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Processes for preparing compounds of the invention are provided as further embodiments of the invention and are illustrated by the following procedures in which the meanings of the generic radicals are as given above unless otherwise qualified.

In cases where compounds are sufficiently basic or acidic, a salt of compounds of the invention can be useful as an intermediate for isolating or purifying compounds of the invention. Additionally, administration of compounds of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1: The synthesis of N-(3,5-difluoro-4-methoxyphenyl)-4-(2-methylimidazo[1,2-c]pyridin-3-yl)thiazol-2-amine hydrochloride (14)

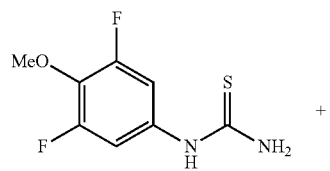

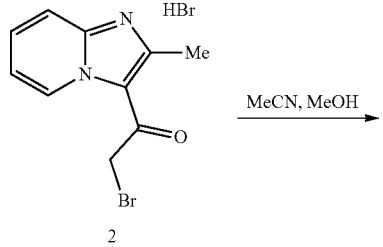

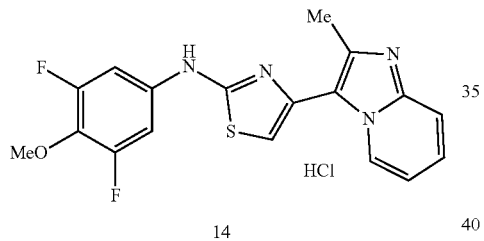

A mixture of 1-(3,5-difluoro-4-methoxyphenyl)thiourea (3) (100 mg, 0.46 mmol, 1.0 eq) and 2-bromo-1-(2-methylimidazo[1,2-c]pyridin-3-yl)ethan-1-one hydrobromide (2) (153 mg, 0.46 mmol, 1.0 eq) in MeCN (7 ml) and MeOH (1 ml) were heated for 3 hours at 70° C. The reaction was determined complete by LC/MS and cooled to room temperature. The reaction was partitioned in (5% MeOH/EtOAc) and NaHCO$_3$(sat, aq). The aqueous was separated and extracted 2× (5% MeOH/EtOAc). The combined organic was washed 1× brine, dried over Na$_2$SO$_4$, filtered and concentrated. The residue was purified by silica gel chromatography (0%→2%→5% MeOH/DCM). The product containing fractions were concentrated and taken up in MeOH. To this solution was added excess 4N HCl in dioxane. The mixture was concentrated and the residue was recrystallized from a mixture of MeOH/EtOAc. The solid was filtered and dried under vacuum to give the title compound (14) (108.1 mg, 100% purity by HPLC) as a white solid. MS: 373.00 [M+H]$^+$. 1H NMR (400 MHz, DMSO-d6) δ 11.05 (s, 1H), 9.10 (dt, J=6.9, 1.1 Hz, 1H), 8.05-7.89 (m, 2H), 7.55-7.49 (m, 2H), 7.48-7.40 (m, 2H), 3.84 (s, 3H), 2.64 (s, 3H).

The intermediate compounds 2 and 3 were prepared as follows.

a. The synthesis of 1-(2-methylimidazo[1,2-a]pyridin-3-yl)ethan-1-one (1)

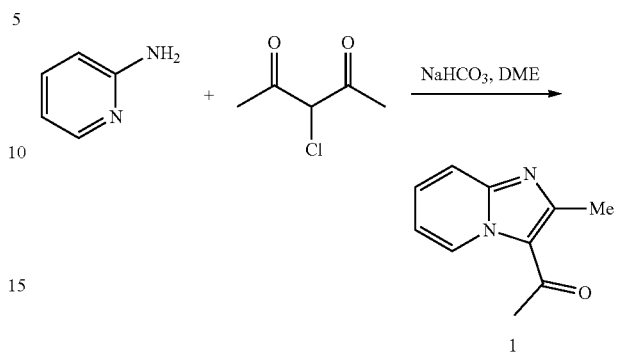

To a suspension of pyridin-2-amine (2.5 g, 26.6 mmol, 1.0 eq) and NaHCO$_3$ (2.34 g, 27.9 mmol, 1.05 eq) in DME (25 ml) was added 3-chloropentane-2,4-dione (4.2 ml, 37.2 mmol, 1.4 eq). The mixture was heated overnight at reflux and cooled to RT. The crude reaction was partitioned in EtOAc/water and the aqueous was extracted 5×EtOAc. The combined organic was dried over Na$_2$SO$_4$, filtered and concentrated. The title compound (1) (2.73 g, 100% purity by HPLC) was isolated as a tan solid after concentration of clean product containing fractions.

b. The synthesis of 2-bromo-1-(2-methylimidazo[1,2-c]pyridin-3-yl)ethan-1-one hydrobromide (2)

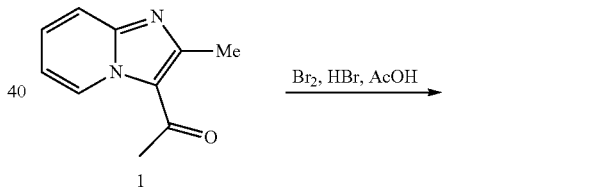

To a solution of 1-(2-methylimidazo[1,2-a]pyridin-3-yl)ethan-1-one (1) (1.0 g, 5.74 mmol, 1.0 eq) in 33% HBr/AcOH (14 ml) was added bromine (323 μl, 6.31 mmol, 1.1 eq). After stirring for 1 hour at room temperature, significant solid had precipitated from solution. The crude reaction was further diluted with Et$_2$O, and stirred for 30 min. The suspension was filtered, washed with Et$_2$O and dried under vacuum to yield (2) (1.94 g, 94% purity by HPLC) as a pale yellow solid. MS: 254.5 [M+H]$^+$.

c. The synthesis of 1-(3,5-difluoro-4-methoxyphenyl)thiourea (3)

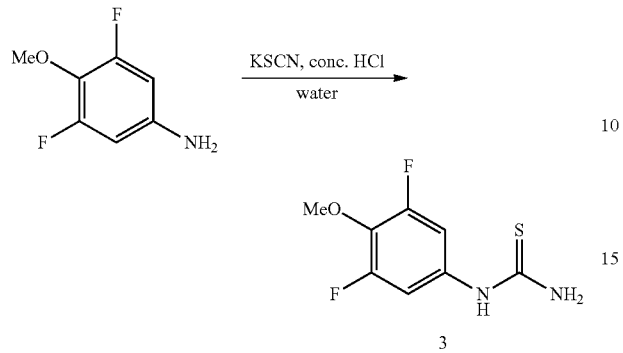

3,5-Difluoro-4-methoxyaniline (500 mg, 3.14 mmol, 1.0 eq) was dissolved in conc. HCl (1 ml) and water (3 ml) and heated for 30 min at reflux. The reaction was cooled to room temperature, at which point KSCN (610 mg, 6.28 mmol, 2.0 eq) was added. The reaction was heated for 4 hours at reflux but showed incomplete conversion by LC/MS. Additional KSCN (400 mg, 4.1 mmol) was added and the reaction was heated overnight at reflux. The reaction was shown to be mostly complete by LC/MS and was cooled to room temperature and diluted with water to precipitate product. The suspension was filtered, washed with water and dried under vacuum. The solid was further recrystallized from MeOH to yield the title compound (3) (206 mg, 90% purity by HPLC) as a yellow solid. MS: 219.05 [M+H]$^+$.

Example 2: The synthesis of N-(4-(methoxy-d$_3$)phenyl)-4-(2-methylimidazo[1,2-c]pyridin-3-yl)thiazol-2-amine hydrochloride (15)

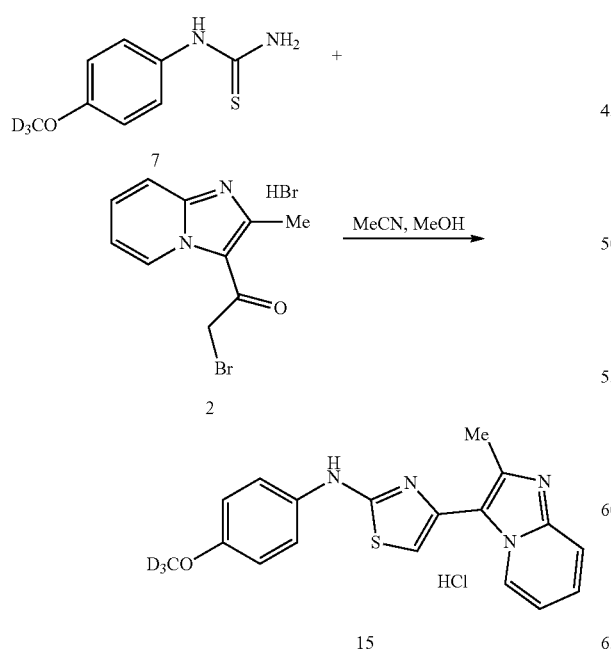

Following the method described for the synthesis of (14), using 1-(4-(methoxy-d$_3$)phenyl)thiourea (7) (85 mg, 0.46 mmol, 1.0 eq) and 2-bromo-1-(2-methylimidazo[1,2-a]pyridin-3-yl)ethan-1-one hydrobromide (2) (153 mg, 0.46 mmol, 1.0 eq), the title compound (15) (80.7 mg, >99% purity by HPLC) was isolated as a light yellow solid. MS: 340.15 [M+H]$^+$. 1H NMR (400 MHz, DMSO-d6) δ 10.46 (s, 1H), 9.19 (dt, J=7.0, 1.1 Hz, 1H), 8.04-7.93 (m, 2H), 7.60-7.52 (m, 3H), 7.38 (s, 1H), 6.96-6.90 (m, 2H), 2.65 (s, 3H).

The intermediate compound 7 was prepared as follows.

a. The synthesis of N-(4-(methoxy-d$_3$)phenyl)acetamide (4)

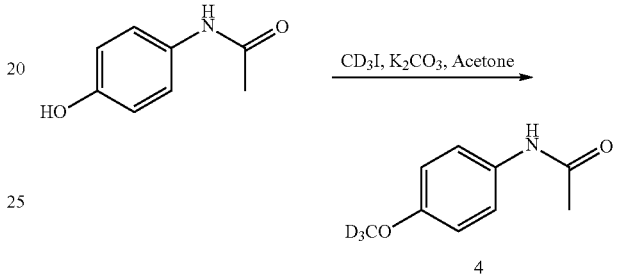

To a solution of N-(4-hydroxyphenyl)acetamide (500 mg, 3.31 mmol, 1.0 eq) in acetone (5 ml) was added K$_2$CO$_3$ (687 mg, 4.97 mmol, 1.5 eq) followed by CD$_3$I (359 μl, 5.63 mmol, 1.7 eq). The reaction was stirred overnight at room temperature and monitored by TLC (50% EtOAc/Hex) to show ~⅔ completion. Additional K$_2$CO$_3$ (300 mg, 2.17 mmol) and CD$_3$I (200 μl, 3.21 mmol) were added and the reaction was stirred for an additional 16 hours. The reaction was shown to be nearly complete by TLC and was partitioned in EtOAc/water. The aqueous was extracted 3×EtOAc and the combined organics were washed 1× brine, dried over Na$_2$SO$_4$, filtered and concentrated. The residue was purified by silica gel chromatography (25%→50% EtOAc/Hex) and product fractions were concentrated under reduced pressure to afford the title compound (4) (479 mg, 100% purity by HPLC) as a white solid. MS: 168.75 [M+H]$^+$.

b. The synthesis of 4-(methoxy-d$_3$)aniline (5)

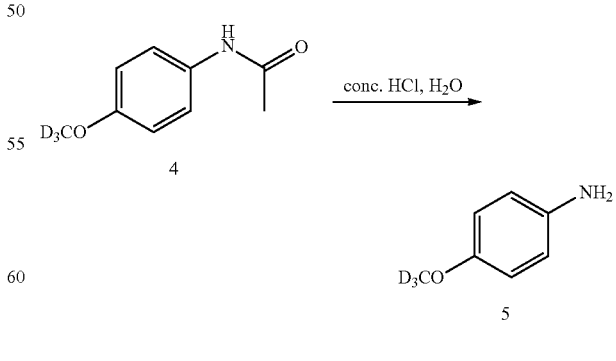

N-(4-(Methoxy-d$_3$)phenyl)acetamide (4) (475 mg, 2.82 mmol, 1 eq) was taken up in a mixture of conc. HCl (5 ml) and water (5 ml). The reaction was heated overnight at 90° C. and determined complete as monitored by LC/MS. The crude reaction was concentrated under reduced pressure to afford product as a white solid which turned brown on standing. Due to reduced purity, the brown solid was partitioned in EtOAc/1N NaOH(aq) and the aqueous was extracted 2×EtOAc. The combined organics were dried over Na₂SO₄, filtered and concentrated. The residue was filtered over a plug of silica gel eluting in (25%→50% EtOAc/Hex) to yield (5) (344 mg) as a brown oil that crystallized into a brown solid on standing. This solid was used as is without further purification.

c. The synthesis of N-((4-(methoxy-d₃)phenyl)carbamothioyl)benzamide (6)

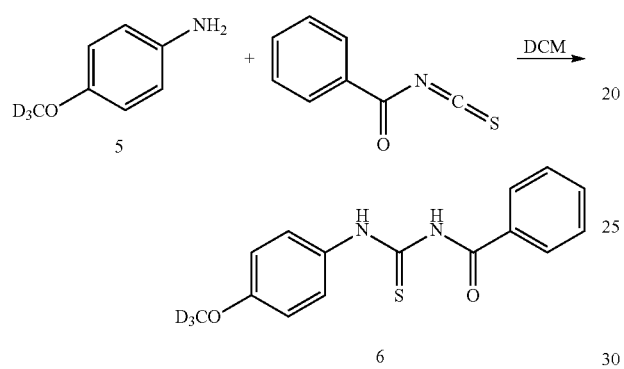

To a solution of 4-(methoxy-d₃)aniline (5) (168 mg, 1.0 mmol, 1.0 eq) in DCM (3 ml) was added benzoyl isothiocyanate (171 mg, 1.05 mmol, 1.05 eq). After 2 hours, the reaction was determined complete by LC/MS and concentrated under reduced pressure. The residue was suspended in Et₂O (5 ml) and stirred overnight. The mixture was sonicated, filtered, washed with Et₂O and the solid was dried under vacuum to afford (6) (267 mg, >99% purity by HPLC) as a tan solid. MS: 289.75 [M+H]⁺.

d. The synthesis of 1-(4-(methoxy-d₃)phenyl)thiourea (7)

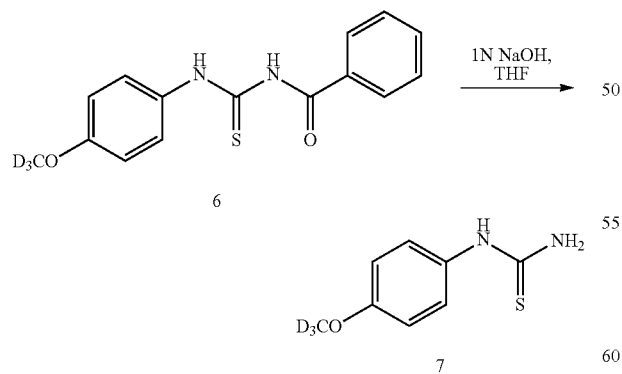

To a solution of N-((4-(methoxy-d₃)phenyl)carbamothioyl)benzamide (6) (267 mg, 0.923 mmol, 1 eq) in THF (3 ml) was added 1N NaOH(aq) (3 ml). The reaction was stirred for 3 hours at 70° C., determined complete by LC/MS and partitioned in EtOAc/water. The organic was separated, washed 1× water, 1× brine, dried over Na₂SO₄, filtered and concentrated to afford (7) (175 mg, 97% purity by HPLC, quantitative yield) as a white solid. MS: 185.65 [M+H]⁺.

Example 3: The synthesis of N-(2,2-difluorobenzo[d][1,3]dioxol-5-yl)-4-(2-methylimidazo[1,2-a]pyridin-3-yl)thiazol-2-amine hydrochloride (16)

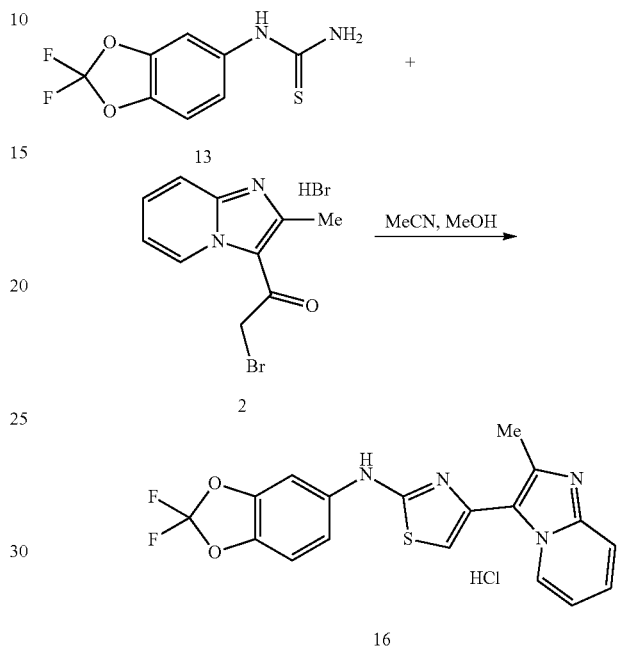

Following the method described for the synthesis of (14), using 1-(2,2-difluorobenzo[d][1,3]dioxol-5-yl)thiourea (13) (145 mg, 0.62 mmol, 1.0 eq) and 2-bromo-1-(2-methylimidazo[1,2-a]pyridin-3-yl)ethan-1-one hydrobromide (2) (208 mg, 0.62 mmol, 1.0 eq), the title compound (16) (174 mg, 100% purity by HPLC) was isolated as a light yellow solid. MS: 386.90 [M+H]⁺. 1H NMR (400 MHz, DMSO-d6) δ 10.97 (s, 1H), 9.10 (dt, J=6.9, 1.1 Hz, 1H), 8.01-7.91 (m, 2H), 7.90 (d, J=2.1 Hz, 1H), 7.52 (td, J=6.7, 1.7 Hz, 1H), 7.49 (s, 1H), 7.37 (d, J=8.8 Hz, 1H), 7.31 (dd, J=8.8, 2.2 Hz, 1H), 2.64 (s, 3H).

The intermediate compound 13 was prepared as follows.

a. The Synthesis of N-((2,2-difluorobenzo[d][1,3]dioxol-5-yl)carbamothioyl)benzamide (12)

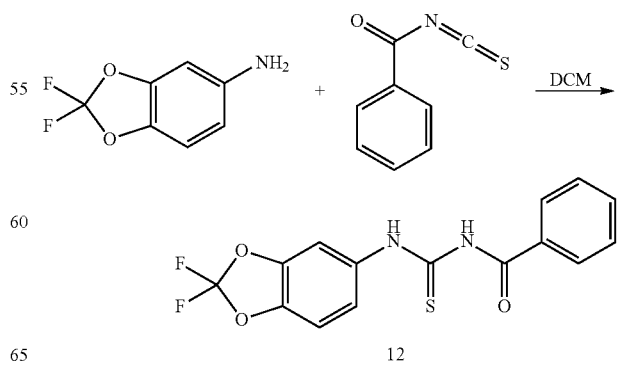

To a solution of 2,2-difluorobenzo[d][1,3]dioxol-5-amine (173 mg, 1.0 mmol, 1.0 eq) in DCM (3 ml) was added benzoyl isothiocyanate (mg, 1.37 mmol, 1.05 eq). After stirring for 1 hour at room temperature, the reaction was determined complete by TLC (25% EtOAc/Hex) and concentrated under reduced pressure. The solid was taken up in Et$_2$O (5 ml), and stirred overnight in a sealed flask. The suspension was filtered, washed with Et$_2$O, and dried under vacuum to afford the title compound (12) (233 mg, 100% purity by HPLC) as a white solid. MS: 336.75 [M+H]$^+$.

b. The Synthesis of 1-(2,2-difluorobenzo[d][1,3]dioxol-5-yl)thiourea (13)

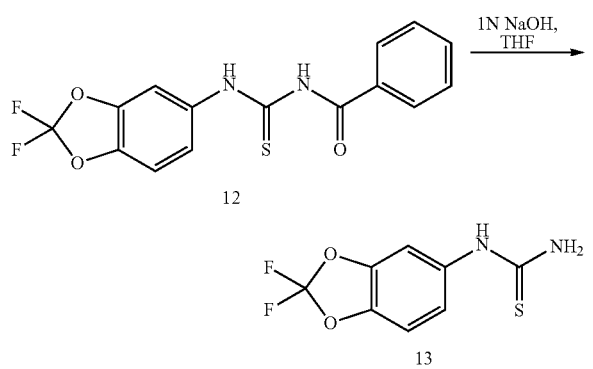

To a solution of N-((2,2-difluorobenzo[d][1,3]dioxol-5-yl)carbamothioyl)benzamide (12) (230 mg, 0.68 mmol, 1.0 eq) in THF (3 ml) was added 1N NaOH (aq) (3 ml). After stirring for 3 hours at 70° C., the reaction was determined complete by LC/MS and partitioned in EtOAc/water. The organic was separated, washed 1× water, 1× brine, dried over Na$_2$SO$_4$, filtered and concentrated to yield (13) (147 mg, 95% purity by HPLC) as a yellow oil. MS: 232.70 [M+H]+.

Example 4: The synthesis of N-(benzo[d][1,3]dioxol-5-yl-2,2-d$_2$)-4-(2-methylimidazo[1,2-c]pyridin-3-yl)thiazol-2-amine hydrochloride (17)

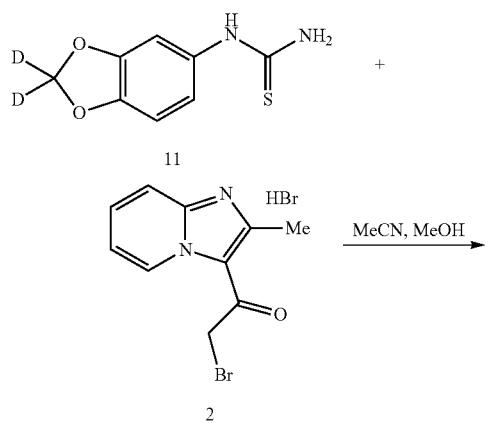

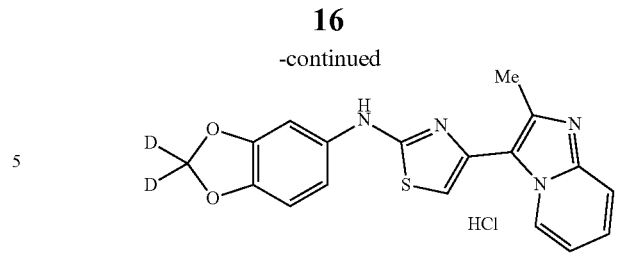

Following the method described for the synthesis of (14), using 1-(benzo[d][1,3]dioxol-5-yl-2,2-d$_2$)thiourea (11) (91 mg, 0.46 mmol, 1.0 eq) and 2-bromo-1-(2-methylimidazo[1,2-a]pyridin-3-yl)ethan-1-one hydrobromide (2) (153 mg, 0.46 mmol, 1.0 eq), the title compound (17) (68 mg, 100% purity by HPLC) was isolated as a white solid. MS: 353.00 [M+H]$^+$. 1H NMR (400 MHz, DMSO-d6) δ 10.51 (s, 1H), 9.14 (dt, J=6.9, 1.1 Hz, 1H), 8.01-7.90 (m, 2H), 7.51 (td, J=6.8, 1.7 Hz, 1H), 7.39 (s, 1H), 7.36 (d, J=2.2 Hz, 1H), 7.01 (dd, J=8.4, 2.2 Hz, 1H), 6.89 (d, J=8.4 Hz, 1H), 2.64 (s, 3H).

The intermediate compound 11 was prepared as follows.

a. The Synthesis of 5-nitrobenzo[d][1,3]dioxole-2,2-d$_2$ (8)

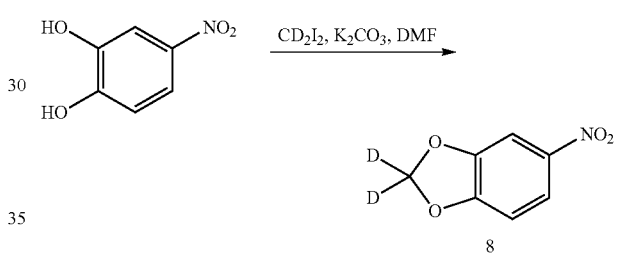

To a solution of 4-nitrobenzene-1,2-diol (500 mg, 3.22 mmol, 1.0 eq) in DMF (12 ml) was added CD$_2$I$_2$ (392 µL, 4.83 mmol, 1.5 eq) followed by K$_2$CO$_3$ (668 mg, 4.83 mmol, 1.5 eq). The reaction was heated overnight at 100° C. in a sealed reaction vessel. Completion was determined by LC/MS and the reaction was cooled to RT and partitioned in EtOAc/water. The organic was separated and washed 2× water, 1× brine, dried over Na$_2$SO$_4$, filtered and concentrated. The crude residue was purified by silica gel chromatography (10%→25% EtOAc/Hex) to afford the title compound (8) (230 mg, 100% purity by HPLC) as a yellow solid. MS: 169.95 [M+H]$^+$.

b. The Synthesis of benzo[d][1,3]dioxol-2,2-d$_{2-5}$-amine (9)

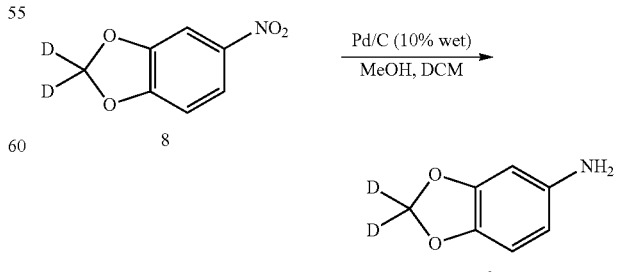

5-Nitrobenzo[d][1,3]dioxole-2,2-d₂ (8) (220 mg, 1.3 mmol, 1.0 eq) in a mixture of MeOH (10 ml) and DCM (10 ml) was (evacuated+backfilled with N₂)×3. Pd/C (10%, wet) (50 mg) was added and the reaction was (evacuated+backfilled with N₂)×2 and (evacuated+backfilled with H2)×3. After stirring for 2 hours under H2 the reaction was confirmed complete by TLC (50% EtOAc/Hex) and filtered over celite. After concentration, the product (9) was isolated as a clear oil that began to turn purple due to air instability. The product was used immediately assuming quantitative yield.

c. The Synthesis of N-((benzo[d][1,3]dioxol-5-yl-2,2-d₂)carbamothioyl)benzamide (10)

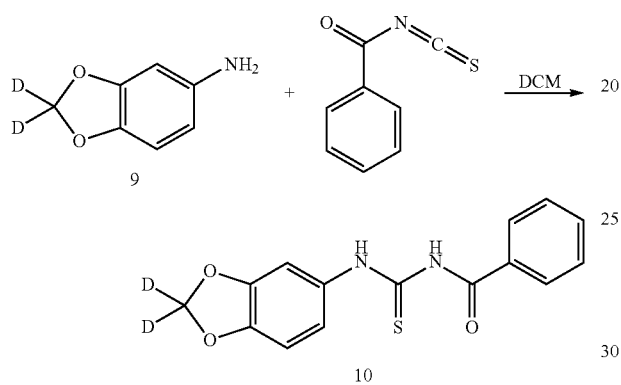

To a solution of benzo[d][1,3]dioxol-2,2-d₂-5-amine (9) (181 mg, 1.3 mmol, 1 eq) in DCM (4 ml) and THF (4 ml) was added benzoyl isothiocyanate (223 mg, 1.37 mmol, 1.05 eq). The reaction was stirred overnight at room temperature and determined complete by LC/MS. The crude reaction was diluted up to 40 ml with hexanes and filtered to remove brown solid impurity. The filtrate was concentrated, recrystallized from MeOH and filtered to afford the title compound (10) (296 mg, 97% purity by HPLC) as a yellow solid. MS: 302.55 [M+H]⁺.

d. The Synthesis of 1-(benzo[d][1,3]dioxol-5-yl-2,2-th)thiourea (11)

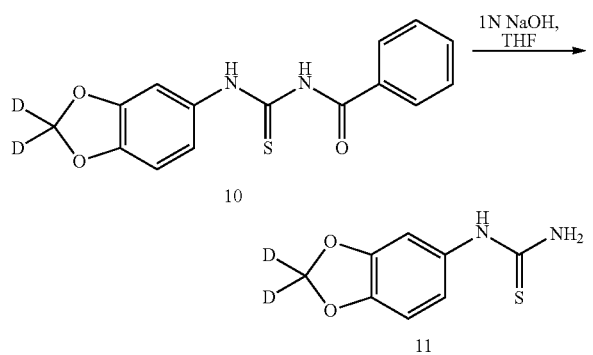

To a solution of N-((benzo[d][1,3]dioxol-5-yl-2,2-th)carbamothioyl)benzamide (10) (292 mg, 0.97 mmol. 1.0 eq) in THF (3 ml) was added 1N NaOH (aq) (3 ml). The reaction was heated for 2 hours at 70° C. and determined complete by LC/MS. Upon cooling to room temperature, a white solid precipitated from solution. The solid was filtered, washed with minimal 1:1 MeOH:water, and dried under vacuum to afford the title compound (11) (182 mg, 98% purity by HPLC) as a white solid. MS: 198.75 [M+H]⁺.

Comparative Example 100: N-(2,4-dimethoxyphenyl)-4-(2-methylimidazo[1,2-a]pyridin-3-yl)thiazol-2-amine

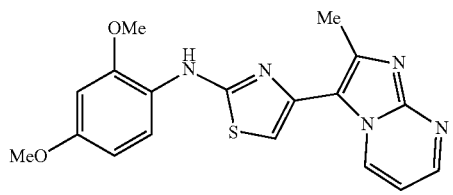 [SMILES: COc1ccc(Nc2nc(-c3c(C)nc4ncccn34)cs2)c(OC)c1]

Comparative Example 101: N-(4-methoxyphenyl)-4-(2-methylimidazo[1,2-a]pyridin-3-yl)thiazol-2-amine

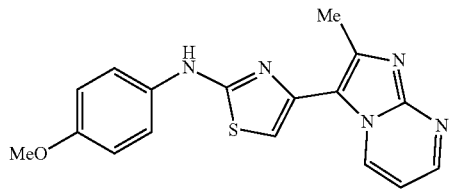 [SMILES: COc1ccc(Nc2nc(-c3c(C)nc4ncccn34)cs2)cc1]

Example 5: MTT Assay

To generate primary patient-derived GBM models for testing small molecule inhibitors, fresh primary tissues were received from patients undergoing surgical resection of WHO grade IV gliomas at Robert Wood Johnson University Hospital (RWJUH) under an approved IRB protocol. De-identified primary human GBM samples were delivered to the laboratory. Cells were obtained through mechanical dissociation of the tumor tissue using a blade and plated in DMEM/F12 medium (Gibco) in the presence of B-27 Supplement (Gibco, #17504-044), 20 ng/ml of human recombinant EGF (Gibco, #PHG0311L) and human recombinant FGF (Peprotech, #AF-100-18B). The following day, the culture was collected, incubated with Accutase (Gibco, #A11105-01) at 37° C. and passed through a 26G×⅜ needle (BD Precision Glide, #305110) to obtain a single cell suspension and re-plated in the same supplemented medium. Cells were cultured at low (5-6) passages in serum-free sphere 3D culture with mitogens that preserve the clonogenic stemness phenotype. Four different primary GBM cells (GBM #46, GBM #50, and GBM #76) were tested for cell viability after treatment with the inhibitors. Cell viability was measured using MTT assay. Briefly, one thousand cells per well were seeded in 96-well plates and exposed to drug in a total of 200 uL media. After 72 hours, 50 uL of stock concentration of 2.5 mg/mL 3-(4,5-dimethylthiazol-2-yl)-2,5-diphenyltetrazolium bromide (MTT) (Sigma, #M2128) dissolved in PBS was added to wells and incubated at 37° C. for 4 hours; read in a fluorescent plate reader at 570 nm and compared to DMSO and untreated cells. The $IC_{50}$ (defined as the concentration at which 50% of the cells were viable) was determined from the curve.

Example 6: Comparison of Exemplary Compound 14 and Comparative Example 100

Small molecules were synthesized by the Molecular Design and Synthesis laboratory, Rutgers Translational Sciences at Rutgers University, NJ, USA. To compare the effects of Exemplary Compound 14 to Comparative Example 100, cells ($3\times10^5$/well) were seeded into the 96-well tissue culture plates and treated with different BMI1 inhibitors (from 10 nM to 10 µM) in appropriate media. Dose response curves were generated upon exposing GBM cells to different concentrations of Exemplary compound 14, Comparative Example 101, and Comparative Example 100 (0.010-10 µM) for 72 hours. Cells were counted using Beckman Coulter Vi-CELL Cell Viability Analyzer, and cell viability was confirmed by CellTiter-Glo Luminescent Cell Viability Assay (Promega, Madison, WI, USA) according to standard protocols and analyzed with a Victor 2 plate reader (Wallac, Turku, Finland). We then assessed the selectivity and potency in GBM cells vs primary GBM. Dose-response curves were generated in both spheres and monocultures and used to determine a sphere selectivity ratio (targeting Glioblastoma Initiating Cells), defined as $EC_{50}(U87)/EC_{50}$ (spheres), for each compound. Compounds that had a sphere selectivity ratio greater than controls (DMSO and Temozolomide) could be defined as agents with high selectivity for glioblastoma cancer stem cells (Exemplary compound 14).

Example 7: Modulation of BMI1

Different GBM cells were treated with DMSO or different concentrations of test compounds for 72 hours. Cells were lysed in Cell Lysis Buffer (Cell Signaling, #9803) supplemented with Protease Inhibitor Cocktail (Sigma, #P8340), spun down for 30 minutes at 4° C., after which the supernatant was collected at every time point indicated. Western blotting analysis was performed on all samples as described above. BMI1 loss started at 6-12 hours, coinciding with an upper shift and hyper-phosphorylation of BMI1 at 12-24 hours and complete depletion at 72 hours. The treatment with these inhibitors caused a dose-dependent reduction in BMI1 and this was also associated with reduction in lysine-119 mono-ubiquitin form of γH2A, a specific product of BMI1 (PRC1) activity.

Example 8: Inhibition of BMI1 Protein Levels by Western Blotting, Performed on 20 Micrograms of Sonicated GBM #46 or GBM #50 Primary Patient Derived Glioblastoma Cells in 3D Spheres Modulate Signaling Pathways in Cell Cycle and Immune Checkpoint Signaling GBM cells were treated with DMSO or different concentrations of the test compounds for 72 hours. Cells were lysed in Cell Lysis Buffer (Cell Signaling, #9803) supplemented with Protease Inhibitor Cocktail (Sigma, #P8340), sonicated briefly while on ice and spun down for 30 minutes at 4° C., after which the supernatant was collected. For each sample, 2 uL of lysate was mixed well into 198 uL de-ionized water. Next, 10 uL of this diluted sample was added to a well in a 96 well plate in quadruplets and mixed with Protein Assay Dye Reagent Concentrate (Bio-Rad, #500-0006) (which was diluted 1:5 with water). BSA standards of 25 ng, 50 ng, 100 ng, 200 ng and 250 ng were also used to the plate and mixed with the reagent. The plate was read in a plate reader at 600 nm and samples were calibrated to the standards to determine the concentration of protein. Using the NuPAGE system (Invitrogen), 25 ug of protein was mixed with NuPAGE LDS 4× Sample Buffer (#NP0007), NuPAGE 10× Reducing Agent (#NP0004) and water, mixed well and heated at 96° C. for 15 minutes to denature the protein. The samples were then loaded into 4-12% Bis-Tris gels (Novex (Invitrogen), #0323) with a protein ladder (Novex (Invitrogen) Sharp Pre-stained protein ladder, #57318) and run at 100-120V for about 2 hours with NuPAGE 20×SDS MES Running Buffer (#NP0002) diluted with water. Next, the gel was taken out and loaded into a NuPAGE transfer cassette with a polyvinylidene membrane with NuPAGE 20× Transfer Buffer (#NP0006-1) diluted with water and methanol. Proteins were transferred for 1 hour at 30V at room temperature. Blocking was performed using the Millipore SNAP i.d. Protein Detection system in 0.25% non-fat dry milk in 0.1% Tween in PBS (PBST). Primary antibodies against BMI1 (Cell Signaling, #6964), mouse monoclonal antiphospho-RB, anti-CDK4, anti-STAT1, anti-PD-L1 (1:1,000) (Millipore), and housekeeping control rabbit polyclonal anti-vinculin (1:1000) (Cell Signaling) were incubated overnight with gentle rocking at 4° C. in the blocking solution. The following day, membranes were washed 3 times with PBST in the SNAP i.d. system before being incubated with secondary antibody in blocking buffer for 1 hour at room temperature. Three washes were then performed in the SNAP i.d. system. Protein signals were detected using ECL Western Blotting Substrate (Pierce, #32106) and filmed.

Novel compounds were synthesized and examined for their effectiveness on inhibiting the growth of patient derived GBM sphere cells that are more enriched in cancer stem-like cells (CSCs). An $IC_{50}$ was established by measuring cell viability using a MTT assay when compared to vehicle control (DMSO) (FIG. 1-6). The $IC_{50}$ was taken after 72 hours of treatment in 96 well plates, and compounds with an $IC_{80}$ greater than or equal to 5 µM were considered to be nonexemplary. Our highly potent new exemplary compounds with $IC_{50}$s against GBM sphere cells at 7-10 nM and when utilized at this highly potent $IC_{50}$s resulted in downregulation of BMI1 protein levels and its downstream effect, Ubiquityl H2A, abolished the clonogenicity of GBM CSCs, and was highly disruptive to the GBM tumorigenic cell cycle.

GBM CSCs are known to be quiescent and therefore resistant to standard chemo/radiotherapy. The retinoblastoma (Rb) tumor suppressor protein regulates cell proliferation by controlling progression through the restriction point within the G1-phase of the cell cycle. Cell cycle-dependent phosphorylation for Ser780 by cyclin D1-CDK4/6 inhibits Rb target binding and allows cell cycle progression. The exemplary compounds that resulted in downregulation of BMI1 also caused downregulation of phospho-RB levels in GBM spheres enriched with CSCs (FIG. 7), providing a potential mechanism for sensitizing CSCs to therapy.

Figure 7:
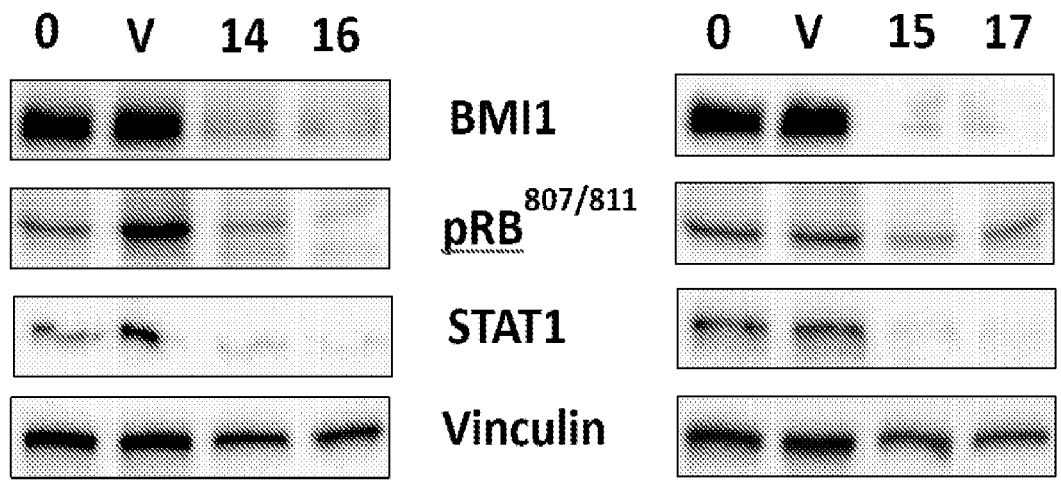
FIG. 7. Shows immune and cell cycle modulating signaling response of glioblastoma patient derived spheres for compounds 14-17 (See Example 7) compound treatment.

Signal transducer and activator of transcription 1 (STAT1) is a transcription factor which in humans is encoded by the STAT1 gene, and is a member of the STAT protein family. STAT1 is phosphorylated by receptor associated kinases that causes STAT1 activation, dimerization and finally translocation to the nucleus to work as transcription factors. STAT1 can be activated by several ligands such as Interferon alpha (IFNα), Interferon gamma (IFNγ), Epidermal Growth Factor (EGF), Platelet Derived Growth Factor (PDGF) or Interleukin 6 (IL-6), all involved in GBM development. STAT1 has a key role in many gene expressions that cause survival of the cell, viability or pathogen response. We demonstrate that the exemplary compounds when used at the same highly potent $IC_{50}$s that resulted in downregulation of BMI1 caused downregulation of STAT1 protein levels (FIG. 7).

Figure 8:
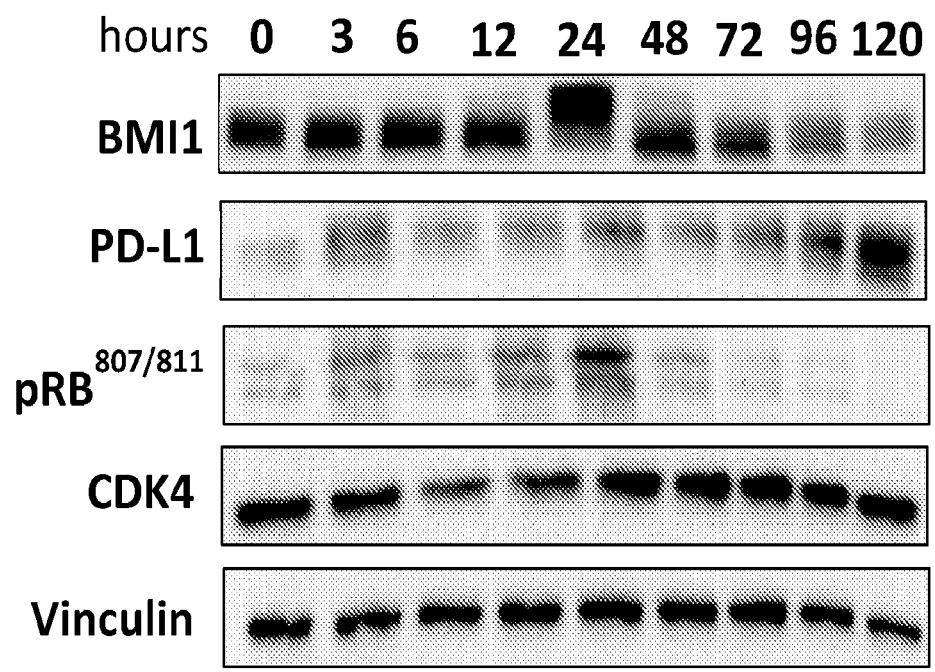
FIG. 8. Shows time course of immune and cell cycle modulating signaling response of glioblastoma patient derived spheres #46 to compound 14 for treatment (See Example 8).

BMI1 levels in GBM spheres were then analyzed by Western Blotting over a time-course of 120 hours upon treatment with compound 14 at 7-10 nM conc. (FIG. 8). A size-shift was observed in BMI1 starting at the 12 hour time point, and maximally seen at the 24 hour time point, followed by reduction in BMI1 protein levels at 72, 96 and 120 hours, from a single treatment, demonstrating a lasting effect. Strikingly, this effect was also correlated with a modulation of the levels of PD-L1 in GBM sphere cells. The programmed death-ligand 1 (PDL1) on tumor cells with its receptor, programmed cell death protein 1 (PD-1) PD-1 on T-lymphocytes are involved in the suppression of the immune system. Immune checkpoint inhibitors such as PD-1 and PD-L1 inhibitors are emerging as a front-line treatment for many cancers. Antibodies against PD-1 and PD-L1 immunotherapies known as checkpoint inhibitors have recently been approved by FDA for several cancer types, however, immunotherapies as a group have off-target effects and toxicities common to them such as interstitial pneumonitis, colitis, skin reactions, immune thrombocytopenia, neutropenia, encephalopathy, Guillain-Barré syndrome, myelitis, myasthenia gravis, myocarditis and cardiac insufficiency, acute adrenal insufficiency, and nephritis. Compound 14 described here modulate of the levels of PD-L1 (FIG. 8) and appear not to have toxicity in vivo when used in preclinical mouse models. Compound 14 that resulted in downregulation of BMI1 also caused downregulation of phospho-RB levels in GBM spheres (FIG. 8) and this downregulation correlated with the levels of cyclin-dependent kinase-4 (CDK4) which is known to induce tumor cell over-proliferation. In conclusion, the highly potent new compound 14 reduce BMI1 protein levels and have activity against GBM tumorigenic cell cycle in GBM spheres and novel immunomodulatory functions through modulating STAT and checkpoint activation.

Example 9: Bi-Directional Caco-2 Transport Assay for Evaluation of Test Compounds as Substrates for Efflux Transporters Efflux transporters (P-gp, MRPs and BCRP) expressed in the intestine play an important role in limiting the entry of xenobiotics into the system. All these transporters are members of ATP-Binding Cassette super family that utilize ATP as an energy source, which allows them to pump substrates against a concentration gradient. Modulation of these transporters can affect the oral bioavailability, biliary and renal clearance, and brain uptake of drugs.

There are several in vitro methods to evaluate if a drug candidate is a substrate of efflux transporters. Out of them, the bi-directional transport assay using Caco-2 cells is regarded as a definitive assay for identifying substrates of efflux transporters, because it measures drug efflux in a more direct manner.

The objective of the study is to evaluate test compounds as substrates for efflux transporter using Caco-2 cell line. To assess the functionality of P-glycoprotein (P-gp), loperamide was run as a positive control (Apical and basolateral HBSS pH 7.4).

5 mM DMSO stock of test compounds and loperamide was diluted 1000-folds in HBSS having 0.1% DMSO to prepare concentrations of 5 µM.

Caco-2 cells were grown in DMEM (20% FBS) until 85-90% confluence. After attaining required confluence, cells were trypsinized and seeded into 24 well millcell plates at a density of $0.6 \times 10^5$ cells/insert. The plates were maintained for 21 days at 37° C. in $CO_2$ incubator with change of medium every alternative day. Monolayer integrity was monitored by measuring Trans-epithelial electrical resistance (TEER) from day 15.

Caco-2 cell monolayer was washed twice with HBSS and incubated for 40 min in $CO_2$ incubator. TEER values were measured and wells showing TEER values above 230 ohms·$cm^2$ were taken for experiments. The study was performed in loperamide and test compounds by adding 400 µL of loperamide prepared in HBSS in apical (A-B transport) followed by addition of 800 µL of HBSS on basal side and for B-A transport 800 µL of loperamide prepared in HBSS was dosed in basal followed by addition of 400 µL HBSS on apical side. At selected time points (0, 15, 30, 60 and 90 mins) an aliquot of 50 µL was collected from the receiver compartment for determination of test compound concentrations. The volume withdrawn was replaced immediately with HBSS buffer. TEER was measured at the end to the experiment to confirm any damage of monolayer while performing experiment. Those wells with TEER not meeting the criteria were excluded from the study.

A 50 µL of test compound samples collected at respective time points and submitted for LC-MS/MS analysis.

The apparent permeability ($P_{app}$) (A–B & B–A) of test compounds and positive control was calculated using the following formula:

$$P_{app} = dQ/dt/A \cdot C_o$$

where, dQ/dt=linear slope of test compound concentration in receptor chamber with time (0, 15, 30, 60 and 90 min) after correcting for dilution; A=area of the filter (0.7 $cm^2$); and $C_o$=initial concentration of compound in the donor compartment.

Efflux ratio ($R_E$) was calculated using the following equation:

$$R_E = P_{B/A}/P_{A/B}$$

where $P_{B/A}$ and $P_{A/B}$ represent the apparent permeability of test compound from the basal to apical and apical to basal side of cell monolayer.

Recovery represents: (amount of the compound recovered from donor at end of incubation+cumulative amount of compound in acceptor at end of incubation+amount of the compound in cell lysate or assay well)/amount of compound in donor solution at time zero*100

Compounds are classified based on $P_{app}$ values as follows:

| | |
|---|---|
| Low | $\leq 3 \times 10^{-6}$ cm/sec |
| Moderate | $3\text{-}15 \times 10^{-6}$ cm/sec |
| High | $>15 \times 10^{-6}$ cm/sec |

A compound having efflux ratio of >2 is considered as having potential as a P-gp substrate.

Figure 9:
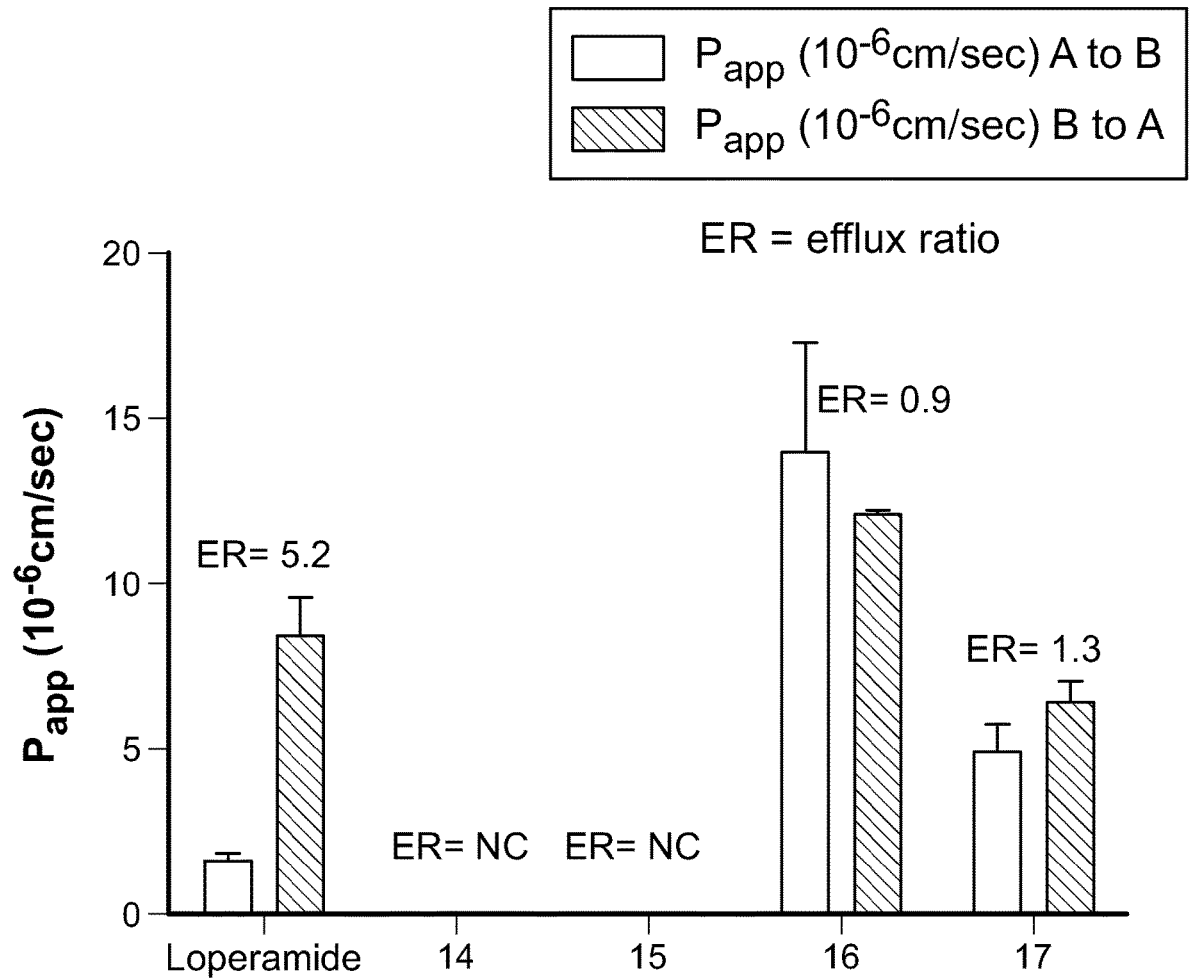
FIG. 9. Shows A-B and B-A permeability ($P_{app}$ $10^{-6}$ cm/sec) and efflux ratios of positive control and test compounds from Example 9.

The integrity of the cell layer was maintained throughout the experiment, as reflected by consistent TEER values before and after the experiment. The P-gp substrate loperamide used in this study showed an efflux ratio of 5.2 indicating that the Caco-2 cells used for the assay has functional P-gp. The summary results ($P_{app}$ and efflux ratio)

of loperamide and test compounds are provided in Table 1 and in FIG. 9. Compounds 14 and 15 showed no/low permeability across Caco-2 cells. Compounds 17 and 16 showed moderate permeability across Caco-2 cells and compounds are not P-gp substrate as shown efflux ratio <2.0.

TABLE 1

Summary of $P_{app}$ and efflux ratios for compounds

| S. No. | Compounds | Papp ($10^{-6}$ cm/sec) | Efflux Ratio (B-A/A-B) |
|---|---|---|---|
| 1 | Loperamide (A-B) | 1.6 ± 0.2 | 5.2 |
|   | Loperamide (B-A) | 8.4 ± 1.2 |     |
| 2 | Compound 14 (A-B) | 0.0 ± 0.0 | — |
|   | Compound 14 (B-A) | 0.0 ± 0.0 |   |
| 3 | Compound 15 (A-B) | 0.0 ± 0.0 | — |
|   | Compound 15 (B-A) | 0.0 ± 0.0 |   |
| 4 | Compound 16 (A-B) | 14.0 ± 3.3 | 0.9 |
|   | Compound 16 (B-A) | 12.1 ± 0.1 |     |
| 5 | Compound 17 (A-B) | 4.9 ± 0.8 | 1.3 |
|   | Compound 17 (B-A) | 6.4 ± 0.6 |     |

Example 10: Metabolic Stability of Test Compounds in Mice Liver Microsomes

Metabolic stability assays using species specific liver microsomes are widely implemented in drug discovery to guide structural modification, predict in vivo performance, develop structure-metabolic stability relationships and triage (sorting) compounds for in vivo animal studies.

The objective of the study was to evaluate the metabolic stability of test compounds in liver microsomes from mice (MLM). This was accomplished by incubating test compounds with microsomes and monitoring disappearance with time using LCMS/MS. Imipramine in MLM was run as positive control.

Potassium phosphate buffer (Kphos) was prepared by adding 0.647 g potassium phosphate monobasic ($KH_2PO_4$) and 3.527 g potassium phosphate dibasic ($K_2HPO_4$) to 400 mL of Milli-Q water. pH of the buffer was adjusted to 7.4 and volume was made up to 500 mL.

Microsomes (20 mg/mL) were diluted in Kphos buffer to prepare a concentration of 0.357 mg/mL.

Stock solutions of test compounds were prepared in DMSO at a concentration of 1 mM.

A stock solution of 3.33 mM NADPH (3.33×) was prepared by dissolving appropriate amount of NADPH in Kphos buffer.

An 1120 µL aliquot of Kphos buffer (50 mM, pH 7.4) containing liver microsomes (0.357 mg/mL) was added to individual 2 mL tubes (final concentration 0.25 mg/mL). Test compounds (1 mM) and positive controls were directly spiked into respective tubes to prepare a concentration of 1.428 µM (final concentration 1 µM). From the above mix, 70 µL was added to individual wells of 96 well reaction plates and pre-incubated at 37° C. for 5 min. All the reactions were initiated by adding 30 µL of 3.33 mM NADPH (final concentration 1 mM). Reactions without NADPH and buffer controls (minus NADPH) at 0 minutes and 60 minutes were also incubated to rule out non-NADPH metabolism or chemical instability in the incubation buffer. All reactions were terminated using 100 µL of ice-cold acetonitrile containing internal standard (glipizide) at 0, 5, 15, 30 and 60 minutes. Plates were centrifuged at 4000 RPM for 15 min and 100 µL aliquots were submitted for analysis by LCMS/MS.

Samples were monitored for parent compounds disappearance in MRM mode using LC-MS/MS.

The percent remaining of test compounds and positive control in each sample was determined by considering peak area ratio in the 0 minute sample as 100%.

The Half-life of compounds in microsomes was calculated by formula: Half-life ($t_{1/2}$) (min)=0.693/k, where k is gradient of line determined from plot of peak area ratio (compound peak area/internal standard peak area) against time.

In vitro intrinsic clearance (CL'int) (units in mL/min/kg) was also calculated. For liver microsomes, scaling factor used was 45 mg microsomal protein per gm liver.

Figure 10A:
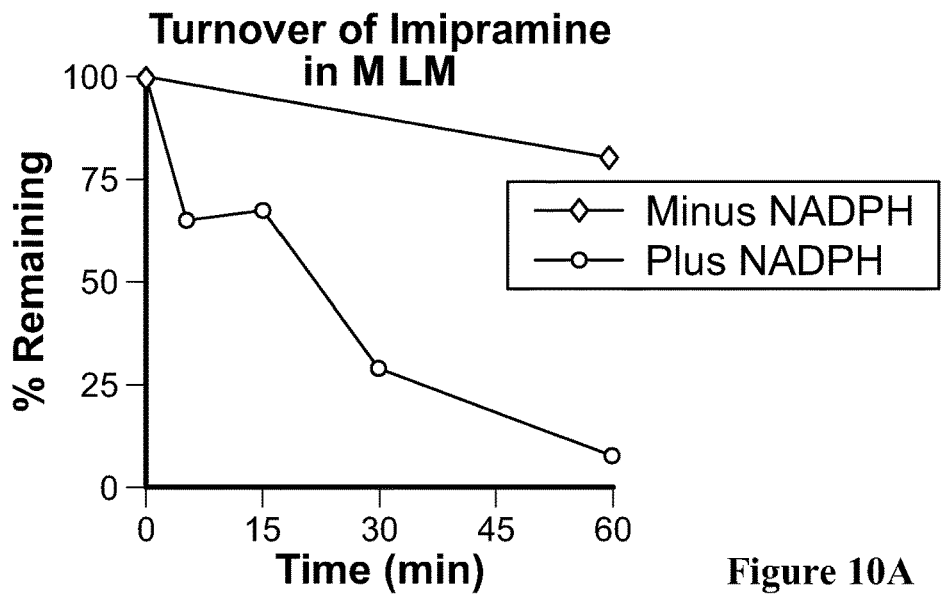
FIG. 10. Shows time-dependent loss of positive control and test compounds in MLM from Example 10.
Figure 10B:
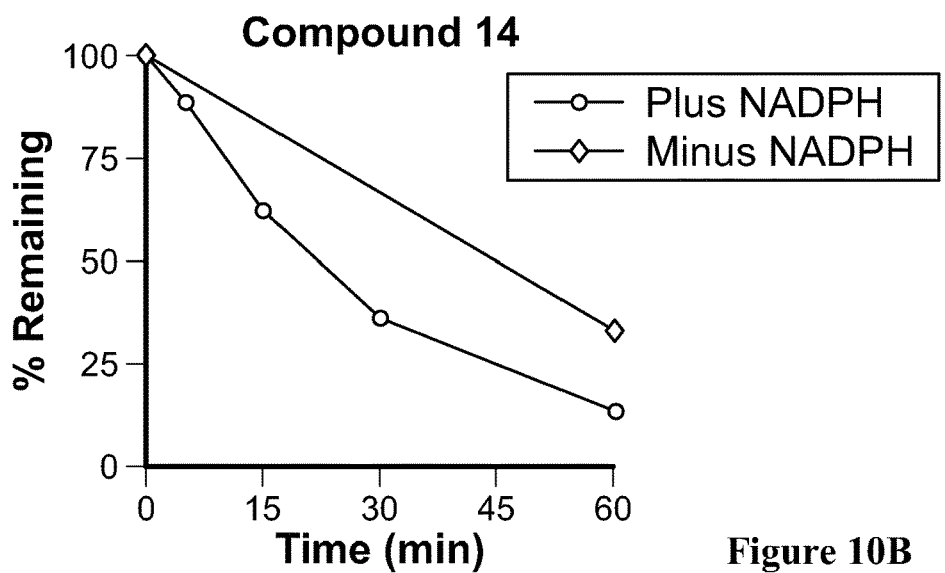
Figure 10C:
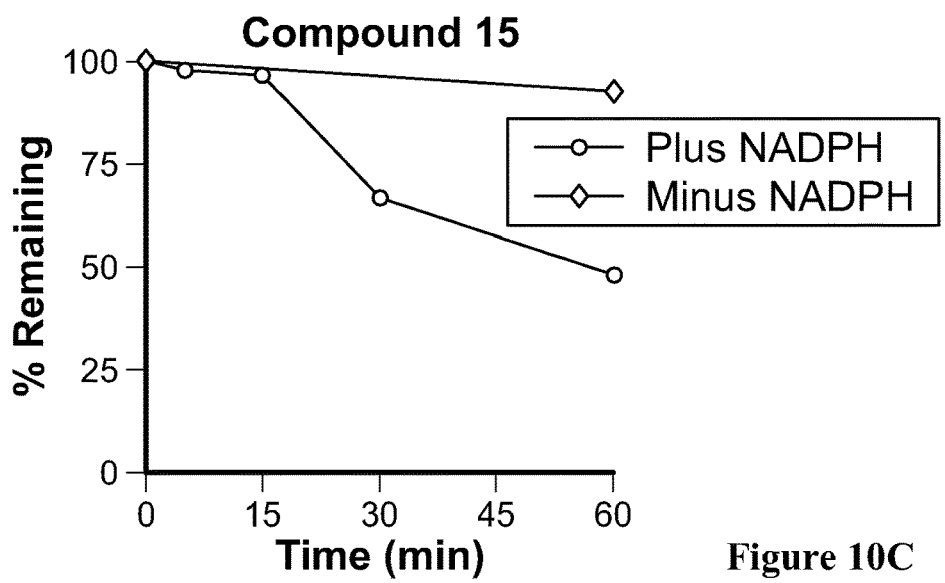
Figure 10D:
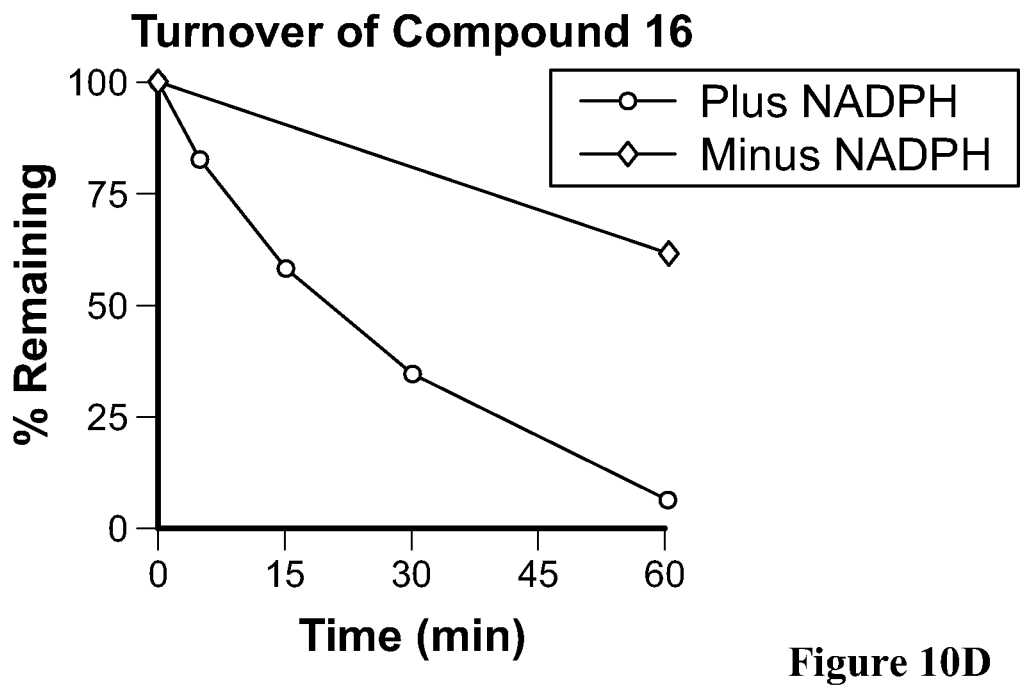
Figure 10E:
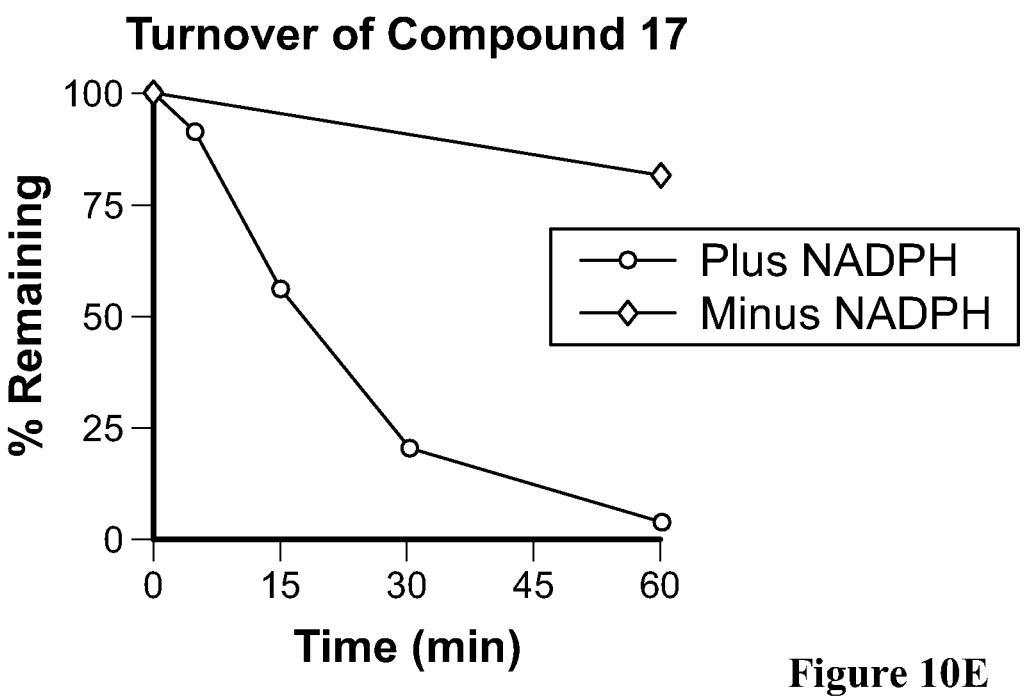

Metabolic stability of positive control compound Imipramine (MLM) used in the experiment were consistent with literature values and validation results (Table 2 and FIG. 10(a)). All compounds showed <50% compound remaining in mice liver microsomes. Details are provided in Table 3-6 and FIGS. 10(b-e).

TABLE 2

Percentage turnover of Imipramine in MLM

| Time (min) | MLM |
|---|---|
| 0 | 100 |
| 5 | 65 |
| 15 | 68 |
| 30 | 28 |
| 60 | 7 |
| % Remaining at 60 min (+NADPH) | 7 |
| % Remaining at 60 min (−NADPH) | 80 |
| % Remaining at 60 min (Buffer) | 106 |
| $t_{1/2}$ (min) | 16 |
| $CL_{h, int}$ (mL/min/kg) | 687 |

TABLE 3

Percentage turnover of Compound 14 in MLM

| Time (min) | MLM |
|---|---|
| 0 | 100 |
| 5 | 88 |
| 15 | 62 |
| 30 | 36 |
| 60 | 13 |
| % Remaining at 60 min (+NADPH) | 13 |
| % Remaining at 60 min (−NADPH) | 33 |
| % Remaining at 60 min (Buffer) | 66 |
| $t_{1/2}$ (min) | 20 |
| $CL_{h, int}$ (mL/min/kg) | 550 |

TABLE 4

Percentage turnover of Compound 15 in MLM

| Time (min) | MLM |
|---|---|
| 0 | 100 |
| 5 | 100 |
| 15 | 98 |
| 30 | 67 |
| 60 | 48 |
| % Remaining at 60 min (+NADPH) | 48 |
| % Remaining at 60 min (−NADPH) | 93 |
| % Remaining at 60 min (Buffer) | 85 |
| $t_{1/2}$ (min) | 52 |
| $CL_{h, int}$ (mL/min/kg) | 215 |

TABLE 5

Percentage turnover of Compound 16 in MLM

| Time (min) | MLM |
|---|---|
| 0 | 100 |
| 5 | 83 |
| 15 | 58 |
| 30 | 35 |
| 60 | 6 |
| % Remaining at 60 min (+NADPH) | 6 |
| % Remaining at 60 min (−NADPH) | 62 |
| % Remaining at 60 min (Buffer) | 87 |
| $t_{1/2}$ (min) | 15 |
| $CL_{h, int}$ (mL/min/kg) | 759 |

TABLE 6

Percentage turnover of Compound 17 in MLM

| Time (min) | MLM |
|---|---|
| 0 | 100 |
| 5 | 91 |
| 15 | 56 |
| 30 | 20 |
| 60 | 3 |
| % Remaining at 60 min (+NADPH) | 3 |
| % Remaining at 60 min (−NADPH) | 81 |
| % Remaining at 60 min (Buffer) | 101 |
| $t_{1/2}$ (min) | 12 |
| $CL_{h, int}$ (mL/min/kg) | 953 |

Example 11: Determination of Protein Binding of Test Compounds in Mice Plasma Using Rapid Equilibrium Dialysis Method Information on drug-plasma protein binding is valuable to evaluate and better understand absorption, distribution, metabolism and excretion (ADME) related properties and the pharmacokinetic profile of drug candidates. It is widely believed that only the free concentration rather than the total drug concentration is pharmacologically active. Plasma protein binding (PPB) data are useful to design optimal dose regimens for efficacy studies and to estimate safety margins during drug development. Many lead molecules with high affinities for a therapeutic target in vitro exhibit a reduced efficacy in vivo. Therefore, the determination of the free fraction (unbound drug) of the drug becomes one of the important issues for both in vitro and in vivo screening of potential drug candidates. Several methods have been applied for the measurement of plasma protein binding including equilibrium dialysis, ultrafiltration and ultracentrifugation combined with LC-MS/MS. Currently, equilibrium dialysis is the most widely used methods for protein binding measurements. Recently, rapid equilibrium dialysis is being applied to determine the protein binding in early drug discovery as several compounds can be evaluated in a high throughput screening mode.

The objective of this study was to evaluate protein binding test compounds in mice plasma. This was accomplished by spiking the test compounds at a concentration of 5 µM into mice plasma and dialyzing against buffer until equilibrium is achieved (4 hours). Analyte area ratios of the test compounds in plasma and buffer were determined to calculate unbound and bound percentages of compound to the plasma proteins.

Phosphate buffered saline pack (0.1 M sodium phosphate and 0.15 M sodium chloride, pH 7.2) was dissolved in 500 mL of deionized water and pH was adjusted to 7.4 with 0.5 N NaOH.

1 mM stock solutions were prepared in DMSO and diluted 200-folds in mice plasma to prepare a concentration of 5 µM. The final DMSO concentration in plasma was 0.5%.

Rapid equilibrium dialysis was performed with a rapid equilibrium dialysis (RED) device containing dialysis membrane with a molecular weight cut-off of 8,000 Daltons. Each dialysis insert contains two chambers. The red chamber is for plasma while the white chamber is for buffer.

A 200 µL aliquot of warfarin and test compound at 5 (triplicates) were separately added to the plasma chamber and 350 µL of phosphate buffer saline (pH 7.4) was added to the buffer chamber of the inserts. After sealing the RED device with an adhesive film, dialysis was performed in incubator at 37° C. with shaking at 100 RPM for 4 hours.

A 50 µL aliquot of warfarin and test compounds were added to four 0.5 mL microfuse tubes. Two aliquots were frozen immediately (0 minute sample). The other two aliquots were incubated at 37° C. for 4 hours along with the RED device.

Following dialysis, an aliquot of 50 µL was removed from each well (both plasma and buffer side) and diluted with equal volume of opposite matrix (dialyzed with the other matrix) to nullify the matrix effect. Similarly, 50 µL of buffer was added to recovery and stability samples. An aliquot of 100 µL was submitted for LCMS/MS analysis.

A 25 µL aliquot of warfarin and test compounds were crashed with 100 µL of acetonitrile containing internal standard (glipizide) and vortexed for 5 minutes. The samples were centrifuged at 4000 RPM at 4° C. for 10 min and 100 µL of supernatant was submitted for LC-MS/MS analysis. Samples were monitored for parent compound in MRM mode using LC-MS/MS.

The peak area ratios (analyte versus internal standard) obtained were used to determine the fraction of compound bound to plasma proteins.

Plasma protein binding (PPB) of positive control warfarin used in the study is consistent with data reported in literature and validation results generated in-house (Table 3). All compounds showed high binding in mice plasma, details provided in Table 7.

TABLE 7

Plasma protein binding of warfarin and test compounds in mice plasma

| Compounds | % Bound | | | | % Recovery | % compound remaining at 4 hrs |
|---|---|---|---|---|---|---|
| | R1 | R2 | R3 | Mean ± SD | | |
| Warfarin | 92.9 | 92.5 | 93.8 | 93.1 ± 0.7 | 109 | 94 |
| 14 | 99.8 | 99.7 | 99.8 | 99.7 ± 0.0 | 124 | 76 |
| 15 | 99.9 | 99.9 | 99.9 | 99.9 ± 0.0 | 114 | 90 |
| 16 | 99.0 | 99.0 | 98.9 | 99.0 ± 0.0 | 117 | 76 |
| 17 | 99.2 | 99.6 | 99.5 | 99.4 ± 0.1 | 124 | 75 |

Example 12: Plasma Pharmacokinetics and Brain Distribution of Compound 15 Following a Single Intravenous (2 mg/kg), Intraperitoneal (10 mg/kg) and Oral (10 Mg/Kg) Administration to Male C57BL/6 Mice The objective of this study was to investigate the plasma pharmacokinetics and brain distribution of Compound (14 in male C57BL/6 mice following a single intravenous, intraperitoneal and oral administration. A group of sixty-three male mice were divided into three groups (Group 1: 2 mg/kg/IV; Group 2: 10 mg/kg/IP and Group 3: 10 mg/kg/PO) with each group comprising of twenty-one mice.

Animals in Group 1 were administered intravenously with Compound 15 solution formulation in 5% NMP, 5% Solutol HS-15, 30% PEG-400 and 60% Captisol (20% w/v) at 2 mg/kg dose. Initially animals were dosed at 10 mg/kg via intravenous route, but mortality was observed in four animals immediately after dose administration. Considering mortality intravenous dose was reduced to 2 mg/kg.

Animals in Group 2 and 3 were administered with Compound 15 solution formulation in 5% NMP, 5% Solutol HS-15, 30% PEG-400 and 60% Captisol (20% w/v) at a dose of 10 mg/kg by intraperitoneal and oral route respectively.

Blood samples (approximately 60 μL) were collected under light isoflurane anesthesia from retro orbital plexus from a set of three mice at 0.08, 0.35, 1, 3, 6, 12 and 24 hr. Plasma samples were separated by centrifugation of whole blood and stored below −70±10° C. until bioanalysis. Immediately after collection of blood, brain samples were collected from set of three mice at each time point. Brain samples were homogenized using ice-cold phosphate buffer saline (pH-7.4) in a ratio of 2 (buffer):1(brain); and homogenates were stored below −70±10° C. until analysis. Total homogenate volume was three times the brain weight. All samples were processed for analysis by protein precipitation using acetonitrile and analyzed with fit-for-purpose LC/MS/MS method (LLOQ2.00 ng/mL for plasma and 3.00 ng/g for brain). Pharmacokinetic parameters were calculated using the non-compartmental analysis tool of Phoenix WinNonlin® (Version 7.0). Pharmacokinetic parameters of Compound 15 are summarized below.

Figure 11:
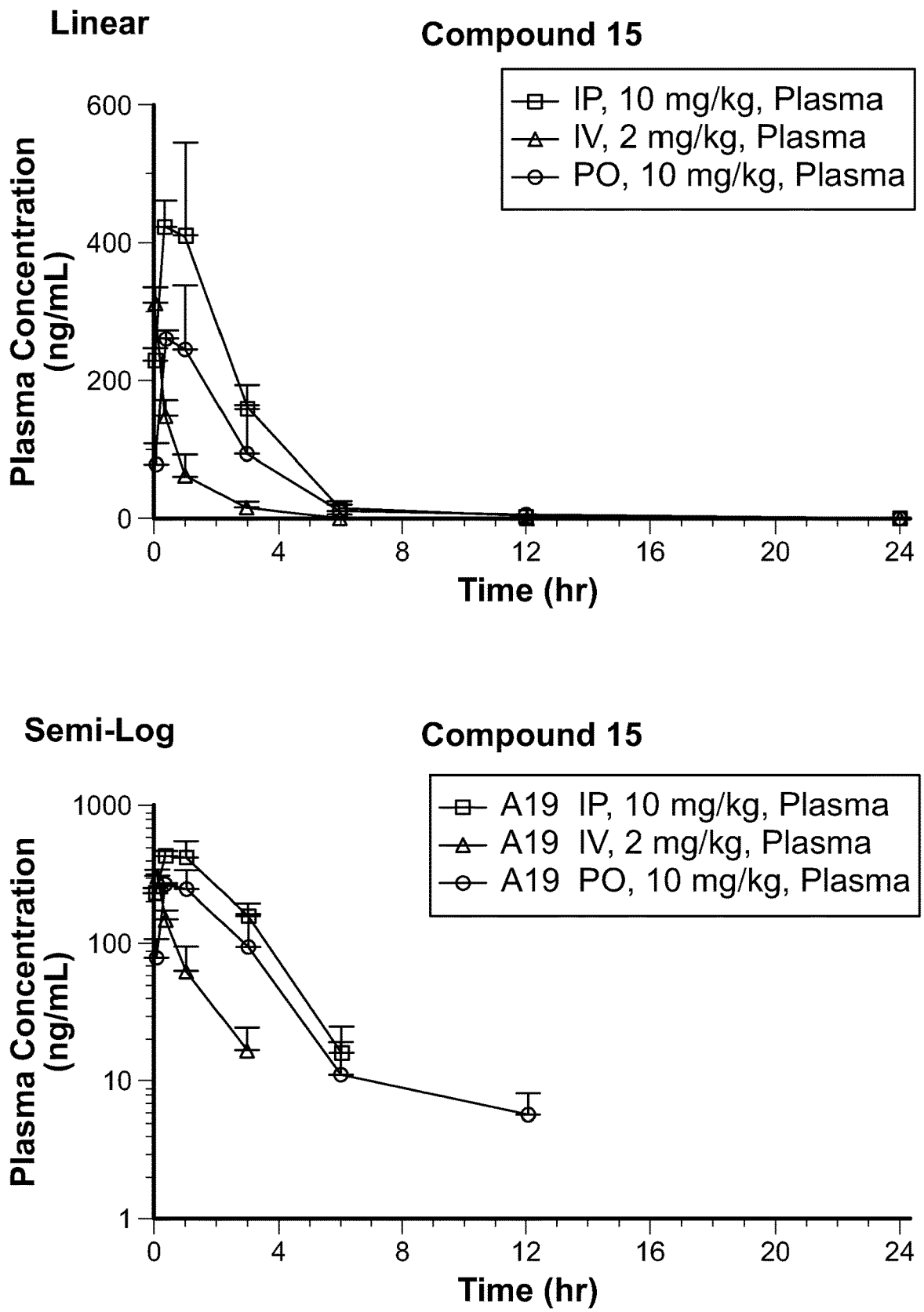
FIG. 11. Shows mean plasma concentration-time profiles of Compound 15 following a single intravenous (Dose: 2 mg/kg), intraperitoneal (Dose: 10 mg/kg) and oral (Dose: 10 mg/kg) administration in male C57BL/6 mice from Example 12.
Figure 12:
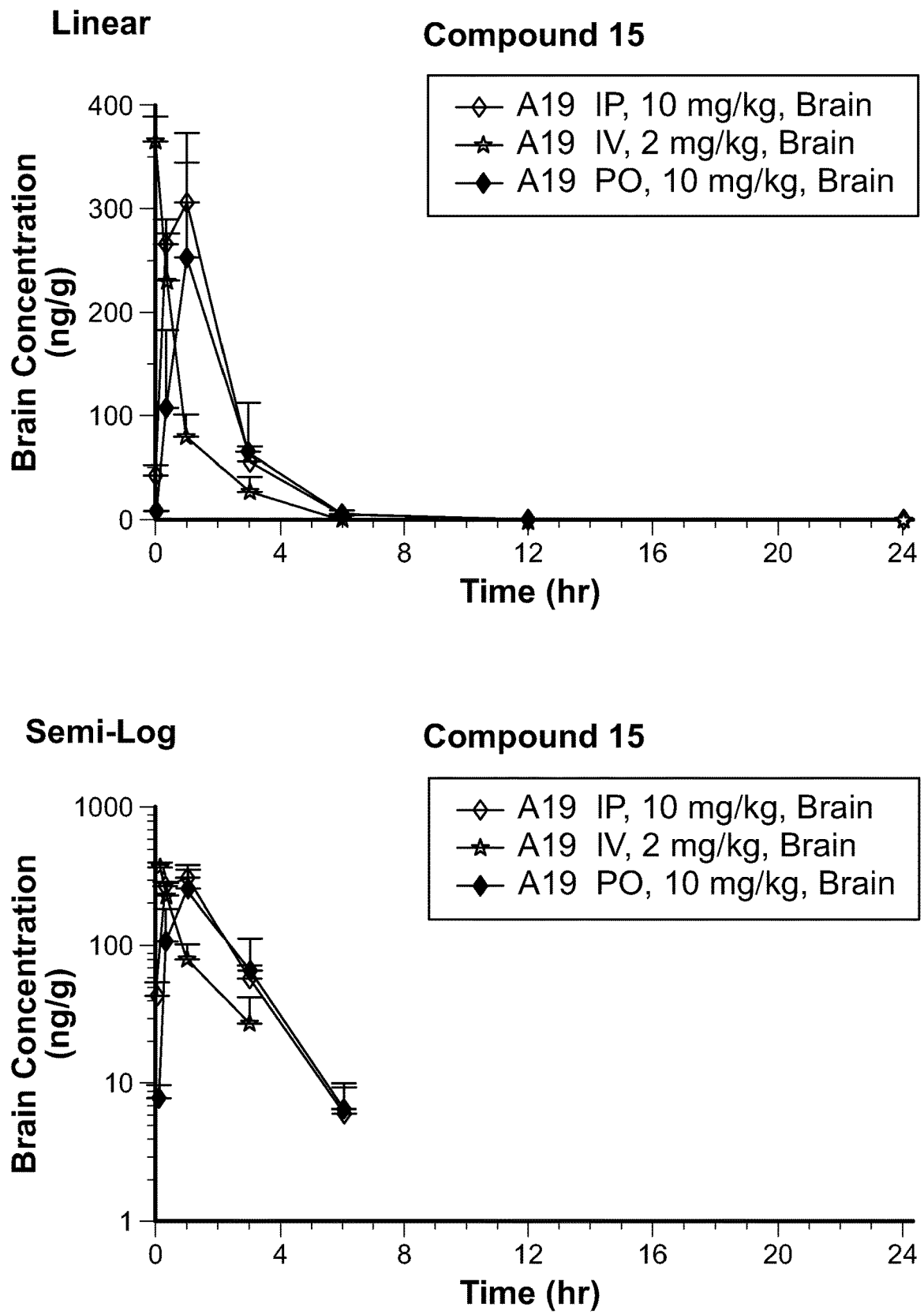
FIG. 12. Shows mean brain concentration-time profiles of Compound 15 following a single intravenous (Dose: 2 mg/kg), intraperitoneal (Dose: 10 mg/kg) and oral (Dose: 10 mg/kg) administration in male C57BL/6 mice from Example 12.

Data for Compound 15 is provided in Tables 8-15 and in FIGS. 11-12.

Table 8 (FIG. 17) shows a summary of mean plasma and brain pharmacokinetic parameters of Compound 15 following a single intravenous (2 mg/kg), intraperitoneal (10 mg/kg) and oral (10 mg/kg) dose administration in male C57BL/6.

Following a single intravenous dose administration of A Compound 15 to male C57BL/6 mice at 2 mg/kg, compound showed high plasma clearance (129.51 mL/min/kg; normal liver blood flow in mice is 90 mL/min/kg) with terminal elimination half-life of 0.88 hr. The Vss was 11-fold more than normal volume of total body water (0.7 L/kg). Brain concentrations were quantifiable up to 3 hr and brain-to-plasma ratio ranged 1.17-1.64.

Following a single intraperitoneal dose administration of Compound 15 to male C57BL/6 mice at 10 mg/kg, plasma concentrations were quantifiable up to 6 hr with $T_{max}$ of 0.35 hr. Brain concentrations were quantifiable up to 6 hr and brain-to-plasma ratio ranged 0.19-0.75.

Following a single oral dose administration of Compound 15 to male C57BL/6 mice at 10 mg/kg, plasma concentrations were quantifiable up to 12 hours with $T_{max}$ of 0.35 hr. Brain concentrations were quantifiable up to 12 hours and brain-to-plasma ratio ranged 0.10-1.03. Oral bioavailability of Compound 15 was 64%.

TABLE 9

Mean brain-to-plasma concentration ratio of Compound 15 following a single intravenous (Dose: 2 mg/kg), intraperitoneal (Dose: 10 mg/kg) and oral (Dose: 10 mg/kg) dose administration in male C57BL/6 mice

| Route | Dose (mg/kg) | Time (hr) | Plasma Conc. (ng/mL) | #Brain Conc. (ng/g) | Brain-to-plasma ratio |
|---|---|---|---|---|---|
| IV | 2 | 0.08 | 312.54 | 366.09 | 1.17 |
|  |  | 0.35 | 148.78 | 230.52 | 1.55 |
|  |  | 1 | 61.85 | 80.05 | 1.29 |
|  |  | 3 | 16.63 | 27.24 | 1.64 |
|  |  | 6 | 0.00 | 0.00 | NA |
|  |  | 12 | 0.00 | 0.00 | NA |
|  |  | 24 | 0.00 | 0.00 | NA |
| IP | 10 | 0.08 | 228.65 | 43.64 | 0.19 |
|  |  | 0.35 | 421.92 | 265.79 | 0.63 |
|  |  | 1 | 408.63 | 305.10 | 0.75 |
|  |  | 3 | 160.38 | 57.71 | 0.36 |
|  |  | 6 | 16.08 | 6.06 | 0.38 |
|  |  | 12 | 0.00 | 0.00 | NA |
|  |  | 24 | 0.00 | 0.00 | NA |
| PO | 10 | 0.08 | 78.19 | 7.99 | 0.10 |
|  |  | 0.35 | 260.65 | 107.69 | 0.41 |
|  |  | 1 | 244.82 | 252.91 | 1.03 |
|  |  | 3 | 93.67 | 65.95 | 0.70 |
|  |  | 6 | 11.10 | 6.63[d] | 0.60 |
|  |  | 12 | 5.82 | 3.63[e] | 0.62 |
|  |  | 24 | 0.00 | 0.00 | NA |

Brain conc. as ng/g, density of brain tissue was considered as 1 which is equivalent to plasma density (1);
NA—Not applicable;
[d]Average of two values considered for analysis;
[e]Single value considered for analysis

TABLE 10

Individual plasma concentration-time data of Compound 15 following a single intravenous administration in male C57BL/6 mice (Dose: 2 mg/kg)

| Animal ID | Plasma concentration (ng/mL) Time (hr) | | | | | | |
|---|---|---|---|---|---|---|---|
|  | 0.08 | 0.35 | 1 | 3 | 6 | 12 | 24 |
| 1 | 338.21 |  |  |  |  |  |  |
| 2 | 298.11 |  |  |  |  |  |  |
| 3 | 301.29 |  |  |  |  |  |  |
| 4 |  | 139.19 |  |  |  |  |  |
| 5 |  | 131.80 |  |  |  |  |  |
| 6 |  | 175.36 |  |  |  |  |  |
| 7 |  |  | 38.70 |  |  |  |  |
| 8 |  |  | 49.39 |  |  |  |  |
| 9 |  |  | 97.47 |  |  |  |  |
| 10 |  |  |  | 8.56 |  |  |  |
| 11 |  |  |  | 23.25 |  |  |  |
| 12 |  |  |  | 18.08 |  |  |  |
| 13 |  |  |  |  | 0.00 |  |  |
| 14 |  |  |  |  | 0.00 |  |  |
| 15 |  |  |  |  | 0.00 |  |  |
| 16 |  |  |  |  |  | 0.00 |  |
| 17 |  |  |  |  |  | 0.00 |  |
| 18 |  |  |  |  |  | 0.00 |  |
| 19 |  |  |  |  |  |  | 0.00 |
| 20 |  |  |  |  |  |  | 0.00 |
| 21 |  |  |  |  |  |  | 0.00 |
| Mean | 312.54 | 148.78 | 61.85 | 16.63 | 0.00 | 0.00 | 0.00 |
| SD | 22.29 | 23.31 | 31.30 | 7.45 | 0.00 | 0.00 | 0.00 |
| CV % | 7.1 | 15.7 | 50.6 | 44.8 | NA | NA | NA |

LLOQ = 2.00 ng/mL;
NA = Not applicable;
No-peaks or values below LLOQ were considered zero

TABLE 11

Individual plasma concentration-time data of Compound 15 following a single intraperitoneal administration in male C57BL/6 mice (Dose: 10 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 22 | 211.42 | | | | | | |
| 23 | 227.57 | | | | | | |
| 24 | 246.97 | | | | | | |
| 25 | | 466.71 | | | | | |
| 26 | | 403.65 | | | | | |
| 27 | | 395.39 | | | | | |
| 28 | | | 563.15 | | | | |
| 29 | | | 358.26 | | | | |
| 30 | | | 304.49 | | | | |
| 31 | | | | 173.61 | | | |
| 32 | | | | 183.31 | | | |
| 33 | | | | 124.22 | | | |
| 34 | | | | | 14.38 | | |
| 35 | | | | | 8.29 | | |
| 36 | | | | | 25.57 | | |
| 37 | | | | | | 0.00 | |
| 38 | | | | | | 0.00 | |
| 39 | | | | | | 0.00 | |
| 40 | | | | | | | 0.00 |
| 41 | | | | | | | 0.00 |
| 42 | | | | | | | 0.00 |
| Mean | 228.65 | 421.92 | 408.63 | 160.38 | 16.08 | 0.00 | 0.00 |
| SD | 17.80 | 39.01 | 136.49 | 31.69 | 8.76 | 0.00 | 0.00 |
| CV % | 7.8 | 9.2 | 33.4 | 19.8 | 54.5 | NA | NA |

LLOQ = 2.00 ng/mL;
NA = Not applicable;
No-peaks or values below LLOQ were considered zero

TABLE 12

Individual plasma concentration-time data of Compound 15 following a single oral administration in male C57BL/6 mice (Dose: 10 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 43 | 55.49 | | | | | | |
| 44 | 66.48 | | | | | | |
| 45 | 112.59 | | | | | | |
| 46 | | 250.63 | | | | | |
| 47 | | 258.84 | | | | | |
| 48 | | 272.48 | | | | | |
| 49 | | | 154.70 | | | | |
| 50 | | | 341.15 | | | | |
| 51 | | | 238.60 | | | | |
| 52 | | | | 166.89 | | | |
| 53 | | | | 90.55 | | | |
| 54 | | | | 23.57 | | | |
| 55 | | | | | 2.02 | | |
| 56 | | | | | 14.05 | | |
| 57 | | | | | 17.24 | | |
| 58 | | | | | | 8.42 | |
| 59 | | | | | | 4.48 | |
| 60 | | | | | | 4.55 | |
| 61 | | | | | | | 0.00 |
| 62 | | | | | | | 0.00 |
| 63 | | | | | | | 0.00 |
| Mean | 78.19 | 260.65 | 244.82 | 93.67 | 11.10 | 5.82 | 0.00 |
| SD | 30.30 | 11.04 | 93.38 | 71.71 | 8.03 | 2.25 | 0.00 |
| CV % | 38.7 | 4.2 | 38.1 | 76.6 | 72.3 | 38.8 | NA |

LLOQ = 2.00 ng/mL;
NA = Not applicable;
No-peaks or values below LLOQ were considered zero

TABLE 13

Individual brain (ng/g) concentration-time data of Compound 15 following a single intravenous administration in male C57BL/6 mice (Dose: 2 mg/kg)

| Animal ID | [#]Brain concentration (ng/g) Time (hr) | | | | | | |
|---|---|---|---|---|---|---|---|
| | 0.08 | 0.35 | 1 | 3 | 6 | 12 | 24 |
| 1 | 352.23 | | | | | | |
| 2 | 392.10 | | | | | | |
| 3 | 353.94 | | | | | | |
| 4 | | 269.55 | | | | | |
| 5 | | 241.32 | | | | | |
| 6 | | 180.69 | | | | | |
| 7 | | | 67.17 | | | | |
| 8 | | | 67.41 | | | | |
| 9 | | | 105.57 | | | | |
| 10 | | | | 11.43 | | | |
| 11 | | | | 42.36 | | | |
| 12 | | | | 27.93 | | | |
| 13 | | | | | 0.00 | | |
| 14 | | | | | 0.00 | | |
| 15 | | | | | 0.00 | | |
| 16 | | | | | | 0.00 | |
| 17 | | | | | | 0.00 | |
| 18 | | | | | | 0.00 | |
| 19 | | | | | | | 0.00 |
| 20 | | | | | | | 0.00 |
| 21 | | | | | | | 0.00 |
| Mean | 366.09 | 230.52 | 80.05 | 27.24 | 0.00 | 0.00 | 0.00 |
| SD | 22.54 | 45.40 | 22.10 | 15.48 | 0.00 | 0.00 | 0.00 |
| CV % | 6.2 | 19.7 | 27.6 | 56.8 | NA | NA | NA |

LLOQ = 3.00 ng/g,
NA—Not applicable;
No peaks or values below LLOQ were considered zero
[#]Brain conc. as ng/g, density of brain tissue was considered as 1 which is equivalent to plasma density (1)

TABLE 14

Individual brain (ng/g) concentration-time data of Compound 15 following a single intraperitoneal administration in male C57BL/6 mice (Dose: 10 mg/kg)

| Animal ID | [#]Brain concentration (ng/g) Time (hr) | | | | | | |
|---|---|---|---|---|---|---|---|
| | 0.08 | 0.35 | 1 | 3 | 6 | 12 | 24 |
| 22 | 55.11 | | | | | | |
| 23 | 38.37 | | | | | | |
| 24 | 37.44 | | | | | | |
| 25 | | 287.49 | | | | | |
| 26 | | 268.08 | | | | | |
| 27 | | 241.80 | | | | | |
| 28 | | | 382.77 | | | | |
| 29 | | | 261.72 | | | | |
| 30 | | | 270.81 | | | | |
| 31 | | | | 48.39 | | | |
| 32 | | | | 72.39 | | | |
| 33 | | | | 52.35 | | | |
| 34 | | | | | 5.55 | | |
| 35 | | | | | 3.00 | | |
| 36 | | | | | 9.63 | | |
| 37 | | | | | | 0.00 | |
| 38 | | | | | | 0.00 | |
| 39 | | | | | | 0.00 | |
| 40 | | | | | | | 0.00 |
| 41 | | | | | | | 0.00 |
| 42 | | | | | | | 0.00 |
| Mean | 43.64 | 265.79 | 305.10 | 57.71 | 6.06 | 0.00 | 0.00 |
| SD | 9.94 | 22.93 | 67.42 | 12.87 | 3.34 | 0.00 | 0.00 |
| CV % | 22.8 | 8.6 | 22.1 | 22.3 | 55.2 | NA | NA |

LLOQ = 3.00 ng/g,
NA—Not applicable;
No peaks or values below LLOQ were considered zero
[#]Brain conc. as ng/g, density of brain tissue was considered as 1 which is equivalent to plasma density (1),

TABLE 15

Individual brain (ng/g) concentration-time data of Compound 15 following a single oral administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| 43 | 6.21 | | | | | | |
| 44 | 8.31 | | | | | | |
| 45 | 9.45 | | | | | | |
| 46 | | 50.19 | | | | | |
| 47 | | 193.95 | | | | | |
| 48 | | 78.93 | | | | | |
| 49 | | | 190.32 | | | | |
| 50 | | | 358.77 | | | | |
| 51 | | | 209.64 | | | | |
| 52 | | | | 111.57 | | | |
| 53 | | | | 67.53 | | | |
| 54 | | | | 18.75 | | | |
| 55 | | | | | 0.00 | | |
| 56 | | | | | 4.32 | | |
| 57 | | | | | 8.94 | | |
| 58 | | | | | | 0.00 | |
| 59 | | | | | | 0.00 | |
| 60 | | | | | | 3.63 | |
| 61 | | | | | | | 0.00 |
| 62 | | | | | | | 0.00 |
| 63 | | | | | | | 0.00 |
| Mean | 7.99 | 107.69 | 252.91 | 65.95 | 6.63$^d$ | 3.63$^c$ | 0.00 |
| SD | 1.64 | 76.07 | 92.18 | 46.43 | NA | NA | 0.00 |
| CV % | 20.6 | 70.6 | 36.4 | 70.4 | NA | NA | NA |

LLOQ = 3.00 ng/g,
NA—Not applicable;
$^d$Average of two values considered for data analysis
$^c$Value excluded from data analysis
Brain conc. as ng/g, density of brain tissue was considered as 1 which is equivalent to plasma density (1),
No peaks or values below LLOQ were considered zero Example 13: Plasma Pharmacokinetics and Brain Distribution of Compound 16 Following a Single Intravenous (10 mg/kg), Intraperitoneal (10 mg/kg) and Oral (10 mg/kg) Administration to Male C57BL/6 Mice The objective of this study was to investigate the plasma pharmacokinetics and brain distribution of Compound 16 in male C57BL/6 mice following a single intravenous, intraperitoneal and oral administration. A group of sixty-three male mice were divided into three groups (Group 1: 10 mg/kg/IV; Group 2: 10 mg/kg/IP and Group 3: 10 mg/kg/PO) with each group comprising of twenty-one mice.

Animals in Group 1 were administered intravenously with Compound 16 solution formulation in 5% NMP, 5% Solutol HS-15 and 90% normal saline at 10 mg/kg dose.

Animals in Group 2 and 3 were administered with Compound 16 solution formulation in 5% NMP, 5% Solutol HS-15 and 90% normal saline at a dose of 10 mg/kg by intraperitoneal and oral route respectively.

Blood samples (approximately 60 μL) were collected under light isoflurane anesthesia from retro orbital plexus from a set of three mice at 0.08, 0.35, 1, 3, 6, 12 and 24 hr. Plasma samples were separated by centrifugation of whole blood and stored below −70±10° C. until bioanalysis. Immediately after collection of blood, brain samples were collected from set of three mice at each time point. Brain samples were homogenized using ice-cold phosphate buffer saline (pH-7.4) in a ratio of 2 (buffer):1(brain); and homogenates were stored below −70±10° C. until analysis. Total homogenate volume was three times the brain weight. All samples were processed for analysis by protein precipitation using acetonitrile and analyzed with fit-for-purpose LC/MS/MS method (LLOQ—1.00 ng/mL for plasma and 3.00 ng/g for brain). Pharmacokinetic parameters were calculated using the non-compartmental analysis tool of Phoenix WinNonlin® (Version 7.0). Pharmacokinetic parameters of Compound 16 are summarized below.

Figure 13:
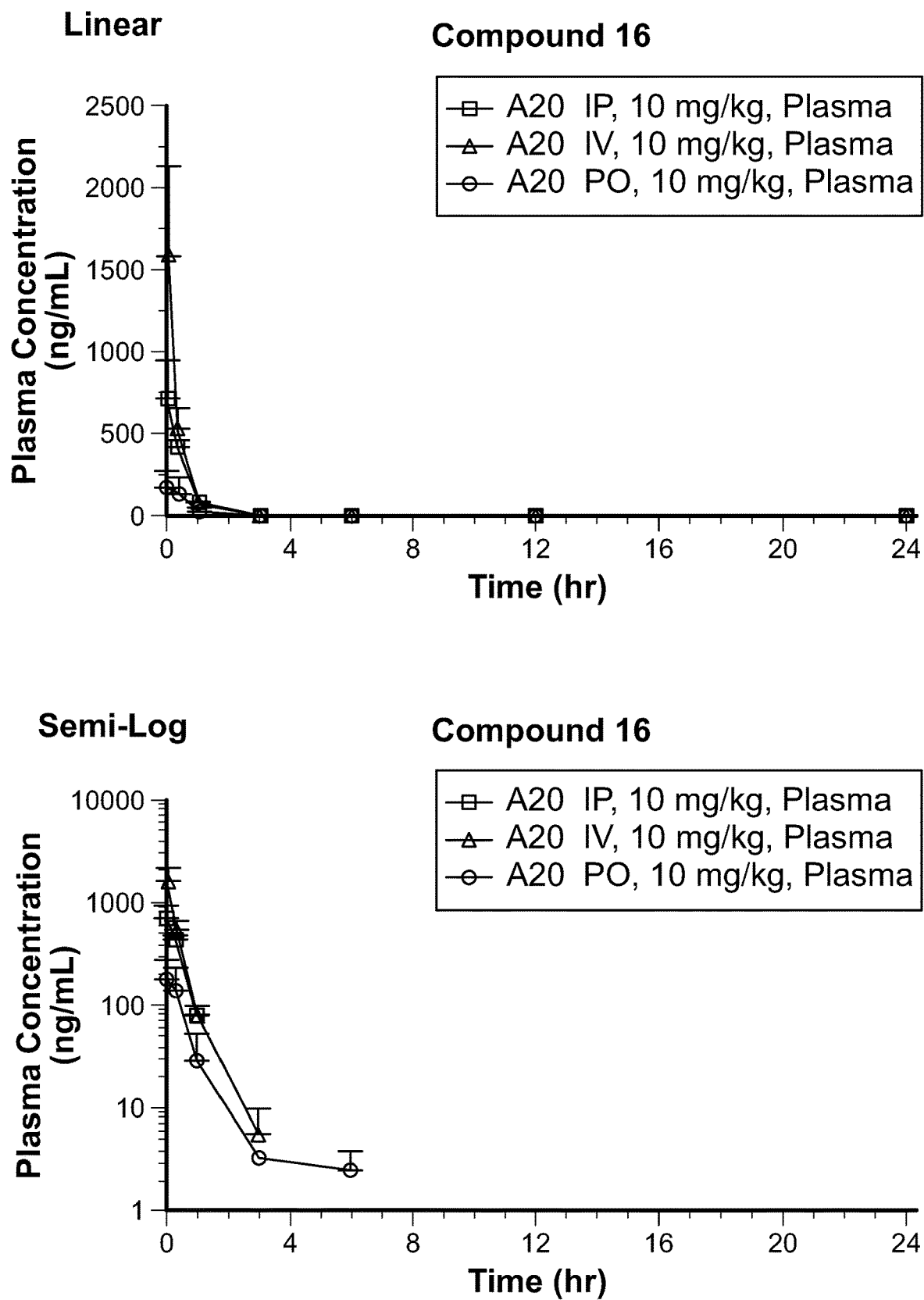
FIG. 13. Shows mean plasma concentration-time profiles of Compound 16 following a single intravenous, intraperitoneal and oral administration in male C57BL/6 mice (Dose: 10 mg/kg) from Example 13.
Figure 14:
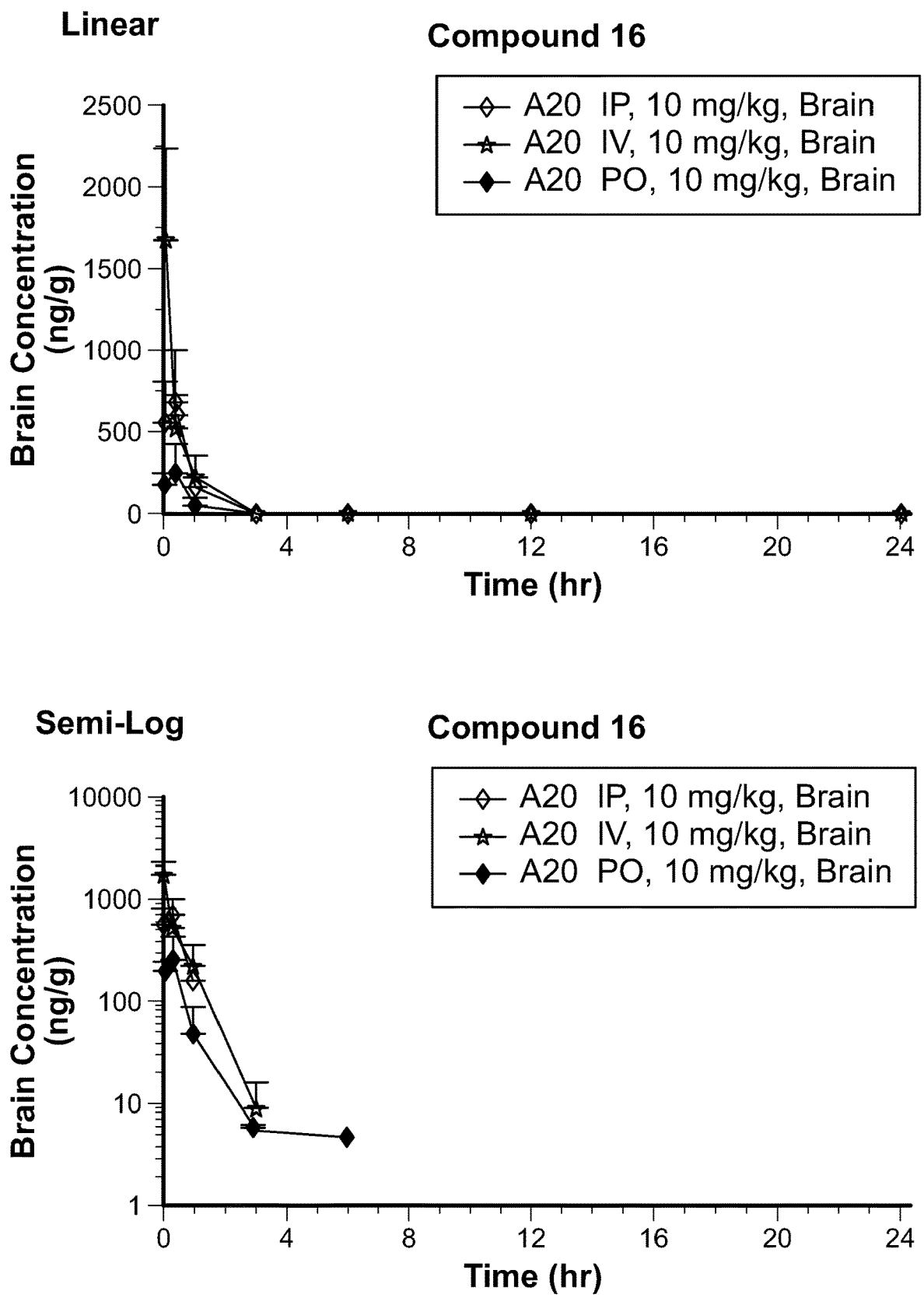
FIG. 14. Shows mean brain concentration-time profiles of Compound 16 following a single intravenous, intraperitoneal and oral administration in male C57BL/6 mice (Dose: 10 mg/kg) from Example 13.

Data for Compound 16 is provided in Tables 16-24 and in FIGS. 13-14.

Table 16 (FIG. 18) shows a summary of mean plasma and brain pharmacokinetic parameters of Compound 16 following a single intravenous (10 mg/kg), intraperitoneal (10 mg/kg) and oral (10 mg/kg) dose administration in male C57BL/6.

Following a single intravenous dose administration of Compound 16 to male C57BL/6 mice at 10 mg/kg, compound showed high plasma clearance (229.73 mL/min/kg; normal liver blood flow in mice is 90 mL/min/kg) with terminal elimination half-life of 0.43 hr. The Vss was 6.6-fold more than normal volume of total body water (0.7 L/kg). Brain concentrations were quantifiable up to 6 hr and brain-to-plasma ratio ranged 0.96-2.78.

Following a single intraperitoneal dose administration of Compound 16 to male C57BL/6 mice at 10 mg/kg, plasma concentrations were quantifiable up to 3 hours with $T_{max}$ of 0.08 hr. Brain concentrations were quantifiable up to 3 hours and brain-to-plasma ratio ranged 0.78-4.34.

Following a single oral dose administration of Compound 16 to male C57BL/6 mice at 10 mg/kg, plasma concentrations were quantifiable up to 6 hours with $T_{max}$ of 0.08 hours. Brain concentrations were quantifiable up to 12 hours and brain-to-plasma ratio ranged 1.07-1.81. Oral bioavailability of Compound 16 was 20%.

TABLE 17

Mean brain-to-plasma concentration ratio of Compound 16 following a single intravenous (Dose: 10 mg/kg), intraperitoneal (Dose: 10 mg/kg) and oral (Dose: 10 mg/kg) dose administration in male C57BL/6 mice

| Route | Dose (mg/kg) | Time (hr) | Plasma Conc. (ng/mL) | #Brain Conc. (ng/g) | Brain-to-plasma ratio |
|---|---|---|---|---|---|
| IV | 10 | 0.08 | 1581.22 | 1661.96 | 1.05 |
| | | 0.35 | 534.74 | 513.95$^d$ | 0.96 |
| | | 1 | 80.65 | 224.59 | 2.78 |
| | | 3 | 5.64 | 9.01 | 1.60 |
| | | 6 | 0.00 | 5.13$^c$ | NA |
| | | 12 | 0.00 | 0.00 | NA |
| | | 24 | 0.00 | 0.00 | NA |
| IP | 10 | 0.08 | 712.56 | 557.83 | 0.78 |
| | | 0.35 | 425.69 | 679.96 | 1.60 |
| | | 1 | 79.10 | 159.25 | 2.01 |
| | | 3 | 1.43$^c$ | 6.21$^c$ | 4.34 |
| | | 6 | 0.00 | 0.00 | NA |
| | | 12 | 0.00 | 0.00 | NA |
| | | 24 | 0.00 | 0.00 | NA |
| PO | 10 | 0.08 | 175.37 | 187.30 | 1.07 |
| | | 0.35 | 138.46 | 253.61 | 1.83 |
| | | 1 | 29.26 | 48.89 | 1.67 |
| | | 3 | 3.35$^c$ | 5.78$^d$ | 1.73 |
| | | 6 | 2.50$^d$ | 4.52$^d$ | 1.81 |
| | | 12 | 0.00 | 3.90$^c$ | NA |
| | | 24 | 0.00 | 0.00 | NA |

Brain conc. as ng/g, density of brain tissue was considered as 1 which is equivalent to plasma density (1);
NA—Not applicable;
$^d$Average of two values considered for analysis;
$^c$Single value considered for analysis

TABLE 18

Individual plasma concentration-time data of Compound 16 following a single intravenous administration in male C57BL/6 mice (Dose: 10 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 1 | 1156.06 | | | | | | |
| 2 | 2189.52 | | | | | | |
| 3 | 1398.08 | | | | | | |
| 4 | | 417.26 | | | | | |
| 5 | | 526.13 | | | | | |
| 6 | | 660.82 | | | | | |
| 7 | | | 60.85 | | | | |
| 8 | | | 93.53 | | | | |
| 9 | | | 87.57 | | | | |
| 10 | | | | 10.61 | | | |
| 11 | | | | 2.41 | | | |
| 12 | | | | 3.89 | | | |
| 13 | | | | | 0.00 | | |
| 14 | | | | | 0.00 | | |
| 15 | | | | | 0.00 | | |
| 16 | | | | | | 0.00 | |
| 17 | | | | | | 0.00 | |
| 18 | | | | | | 0.00 | |
| 19 | | | | | | | 0.00 |
| 20 | | | | | | | 0.00 |
| 21 | | | | | | | 0.00 |
| Mean | 1581.22 | 534.74 | 80.65 | 5.64 | 0.00 | 0.00 | 0.00 |
| SD | 540.52 | 122.01 | 17.40 | 4.37 | 0.00 | 0.00 | 0.00 |
| CV % | 34.2 | 22.8 | 21.6 | 77.5 | NA | NA | NA |

LLOQ = 1.00 ng/mL;
NA = Not applicable;
No-peaks or values below LLOQ were considered zero

TABLE 19

Individual plasma concentration-time data of Compound 16 following a single intraperitoneal administration in male C57BL/6 mice (Dose: 10 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 22 | 497.26 | | | | | | |
| 23 | 687.91 | | | | | | |
| 24 | 952.51 | | | | | | |
| 25 | | 391.07 | | | | | |
| 26 | | 436.80 | | | | | |
| 27 | | 449.20 | | | | | |
| 28 | | | 61.95 | | | | |
| 29 | | | 78.62 | | | | |
| 30 | | | 96.73 | | | | |
| 31 | | | | 0.00 | | | |
| 32 | | | | 1.43 | | | |
| 33 | | | | 0.00 | | | |
| 34 | | | | | 0.00 | | |
| 35 | | | | | 0.00 | | |
| 36 | | | | | 0.00 | | |
| 37 | | | | | | 0.00 | |
| 38 | | | | | | 0.00 | |
| 39 | | | | | | 0.00 | |
| 40 | | | | | | | 0.00 |
| 41 | | | | | | | 0.00 |
| 42 | | | | | | | 0.00 |
| Mean | 712.56 | 425.69 | 79.10 | 1.43[c] | 0.00 | 0.00 | 0.00 |
| SD | 228.62 | 30.62 | 17.39 | NA | 0.00 | 0.00 | 0.00 |
| CV % | 32.1 | 7.2 | 22.0 | NA | NA | NA | NA |

LLOQ = 1.00 ng/mL;
NA = Not applicable;
No-peaks or values below LLOQ were considered zero
[c]Value excluded from data analysis

TABLE 20

Individual plasma concentration-time data of Compound 16 following a single oral administration in male C57BL/6 mice (Dose: 10 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 43 | 124.15 | | | | | | |
| 44 | 291.67 | | | | | | |
| 45 | 110.29 | | | | | | |
| 46 | | 106.25 | | | | | |
| 47 | | 244.67 | | | | | |
| 48 | | 64.47 | | | | | |
| 49 | | | 22.99 | | | | |
| 50 | | | 54.46 | | | | |
| 51 | | | 10.34 | | | | |
| 52 | | | | 3.35 | | | |
| 53 | | | | 0.00 | | | |
| 54 | | | | 0.00 | | | |
| 55 | | | | | 0.00 | | |
| 56 | | | | | 3.53 | | |
| 57 | | | | | 1.47 | | |
| 58 | | | | | | 0.00 | |
| 59 | | | | | | 0.00 | |
| 60 | | | | | | 0.00 | |
| 61 | | | | | | | 0.00 |
| 62 | | | | | | | 0.00 |
| 63 | | | | | | | 0.00 |
| Mean | 175.37 | 138.46 | 29.26 | 3.35[f] | 2.50[d] | 0.00 | 0.00 |
| SD | 100.96 | 94.32 | 22.72 | NA | NA | 0.00 | 0.00 |
| CV % | 57.6 | 68.1 | 77.6 | NA | NA | NA | NA |

LLOQ = 1.00 ng/mL;
NA = Not applicable;
No-peaks or values below LLOQ were considered zero
[f]Single value reported and considered for data analysis
[d]Average of two values considered for data analysis

TABLE 21

Individual brain (ng/g) concentration-time data of Compound 16 following a single intravenous administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| 1 | 1022.61 | | | | | | |
| 2 | 2104.41 | | | | | | |
| 3 | 1858.86 | | | | | | |
| 4 | | 368.04 | | | | | |
| 5 | | 2657.52[e] | | | | | |
| 6 | | 659.85 | | | | | |
| 7 | | | 74.46 | | | | |
| 8 | | | 320.88 | | | | |
| 9 | | | 278.43 | | | | |
| 10 | | | | 17.34 | | | |
| 11 | | | | 4.23 | | | |
| 12 | | | | 5.46 | | | |
| 13 | | | | | 5.13 | | |
| 14 | | | | | 0.00 | | |
| 15 | | | | | 0.00 | | |
| 16 | | | | | | 0.00 | |
| 17 | | | | | | 0.00 | |
| 18 | | | | | | 0.00 | |
| 19 | | | | | | | 0.00 |
| 20 | | | | | | | 0.00 |
| 21 | | | | | | | 0.00 |

TABLE 21-continued

Individual brain (ng/g) concentration-time data of Compound 16 following a single intravenous administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| Mean | 1661.96 | 513.95$^d$ | 224.59 | 9.01 | 5.13$^c$ | 0.00 | 0.00 |
| SD | 567.14 | NA | 131.74 | 7.24 | NA | 0.00 | 0.00 |
| CV % | 34.1 | NA | 58.7 | 80.4 | NA | NA | NA |

LLOQ = 3.00 ng/g,
NA—Not applicable;
No peaks or values below LLOQ were considered zero
$^d$Average of two values considered for data analysis
$^e$Value excluded from data analysis as PK outlier
$^c$Value excluded from data analysis
Brain conc. as ng/g, density of brain tissue was considered as 1 which is equivalent to plasma density (1)

TABLE 22

Individual brain (ng/g) concentration-time data of Compound 16 following a single intraperitoneal administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| 22 | 508.68 | | | | | | |
| 23 | 343.80 | | | | | | |
| 24 | 821.01 | | | | | | |
| 25 | | 416.49 | | | | | |
| 26 | | 576.63 | | | | | |
| 27 | | 1046.76 | | | | | |
| 28 | | | 173.13 | | | | |
| 29 | | | 93.27 | | | | |
| 30 | | | 211.35 | | | | |
| 31 | | | | 0.00 | | | |
| 32 | | | | 6.21 | | | |
| 33 | | | | 0.00 | | | |
| 34 | | | | | 0.00 | | |
| 35 | | | | | 0.00 | | |
| 36 | | | | | 0.00 | | |
| 37 | | | | | | 0.00 | |
| 38 | | | | | | 0.00 | |
| 39 | | | | | | 0.00 | |
| 40 | | | | | | | 0.00 |
| 41 | | | | | | | 0.00 |
| 42 | | | | | | | 0.00 |
| Mean | 557.83 | 679.96 | 159.25 | 6.21$^c$ | 0.00 | 0.00 | 0.00 |
| SD | 242.37 | 327.59 | 60.25 | NA | 0.00 | 0.00 | 0.00 |
| CV % | 43.4 | 48.2 | 37.8 | NA | NA | NA | NA |

LLOQ = 3.00 ng/g,
NA—Not applicable;
No peaks or values below LLOQ were considered zero
$^c$Value excluded from data analysis
Brain conc. as ng/g, density of brain tissue was considered as 1 which is equivalent to plasma density (1),

TABLE 23

Individual brain (ng/g) concentration-time data of Compound 16 following a single oral administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| 43 | 225.54 | | | | | | |
| 44 | 221.01 | | | | | | |
| 45 | 115.35 | | | | | | |
| 46 | | 196.68 | | | | | |
| 47 | | 444.18 | | | | | |
| 48 | | 119.97 | | | | | |
| 49 | | | 22.86 | | | | |
| 50 | | | 94.23 | | | | |
| 51 | | | 29.58 | | | | |
| 52 | | | | 6.03 | | | |
| 53 | | | | 5.52 | | | |
| 54 | | | | 0.00 | | | |
| 55 | | | | | 0.00 | | |
| 56 | | | | | 4.74 | | |
| 57 | | | | | 4.29 | | |
| 58 | | | | | | 0.00 | |
| 59 | | | | | | 0.00 | |
| 60 | | | | | | 3.90 | |
| 61 | | | | | | | 0.00 |
| 62 | | | | | | | 0.00 |
| 63 | | | | | | | 0.00 |
| Mean | 187.30 | 253.61 | 48.89 | 5.78$^d$ | 4.52$^d$ | 3.90$^c$ | 0.00 |
| SD | 62.35 | 169.44 | 39.41 | NA | NA | NA | 0.00 |
| CV % | 33.3 | 66.8 | 80.6 | NA | NA | NA | NA |

LLOQ = 3.00 ng/g,
NA—Not applicable;
$^d$Average of two values considered for data analysis
$^c$Value excluded from data analysis
Brain conc. as ng/g, density of brain tissue was considered as 1 which is equivalent to plasma density (1),
No peaks or values below LLOQ were considered zero Example 14: Plasma Pharmacokinetics and Brain Distribution of Compound 17 Following a Single Intravenous (2 mg/kg), Intraperitoneal (10 mg/kg) and Oral (10 mg/kg) Administration to Male C57BL/6 Mice The objective of this study was to investigate the plasma pharmacokinetics and brain distribution of Compound 17 in male C57BL/6 mice following a single intravenous, intraperitoneal and oral administration. A group of sixty-three male mice were divided into three groups (Group 1: 2 mg/kg/IV; Group 2: 10 mg/kg/IP and Group 3: 10 mg/kg/PO) with each group comprising of twenty-one mice.

Animals in Group 1 were administered intravenously with Compound 17 solution formulation in 5% NMP, 5% Solutol HS-15, 30% PEG-400 and 60% normal saline at 2 mg/kg dose. Initially animals were dosed at 10 mg/kg via intravenous route, but mortality was observed in six animals immediately after dose administration. Considering mortality dose was reduced to 2 mg/kg.

Animals in Group 2 and 3 were administered with Compound 17 solution formulation in 5% NMP, 5% Solutol HS-15, 30% PEG-400 and 60% normal saline at a dose of 10 mg/kg by intraperitoneal and oral route respectively.

Blood samples (approximately 60 µL) were collected under light isoflurane anesthesia from retro orbital plexus from a set of three mice at 0.08, 0.35, 1, 3, 6, 12 and 24 hr. Plasma samples were separated by centrifugation of whole blood and stored below −70±10° C. until bioanalysis. Immediately after collection of blood, brain samples were collected from set of three mice at each time point. Brain samples were homogenized using ice-cold phosphate buffer saline (pH-7.4) in a ratio of 2 (buffer):1(brain); and homogenates were stored below −70±10° C. until analysis. Total homogenate volume was three times the brain weight. All samples were processed for analysis by protein precipitation using acetonitrile and analyzed with fit-for-purpose LC/MS/MS method (LLOQ—2.01 ng/mL for plasma and 3.00 ng/g for brain). Pharmacokinetic parameters were calculated using the non-compartmental analysis tool of Phoenix WinNonlin® (Version 7.0). Pharmacokinetic parameters of Compound 17 are summarized below.

Figure 15:
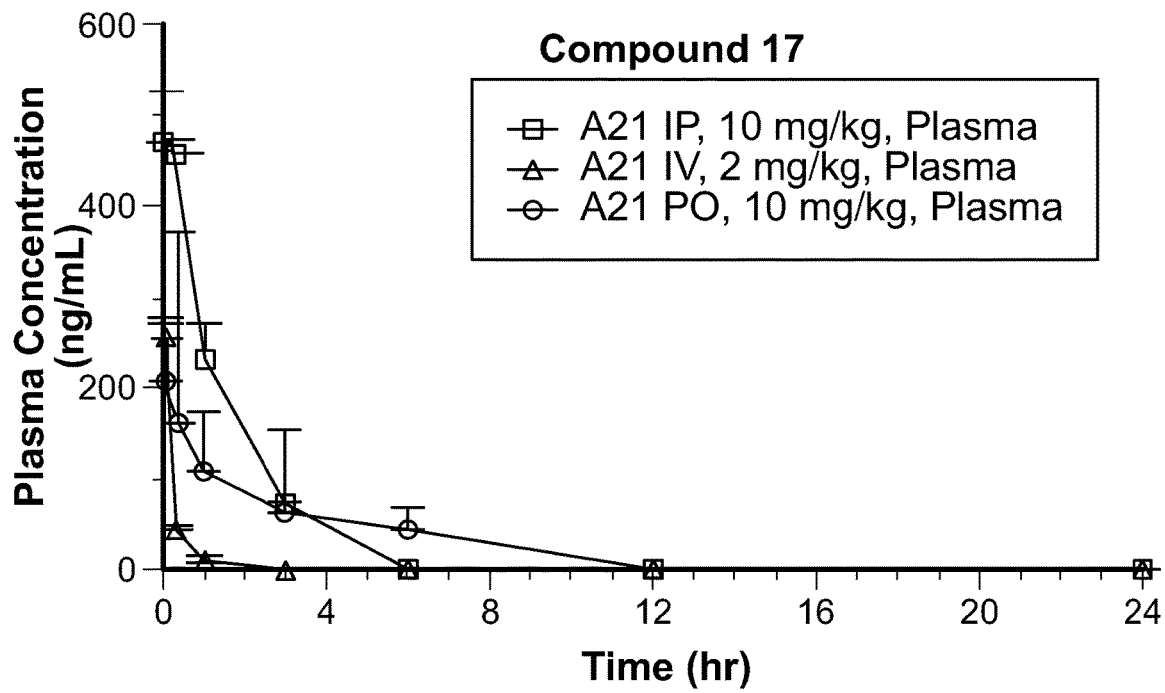
FIG. 15. Shows mean plasma concentration-time profiles of Compound 17 following a single intravenous (Dose: 2 mg/kg), intraperitoneal (Dose: 10 mg/kg) and oral (Dose: 10 mg/kg) administration in male C57BL/6 mice from Example 14.
Figure 15:
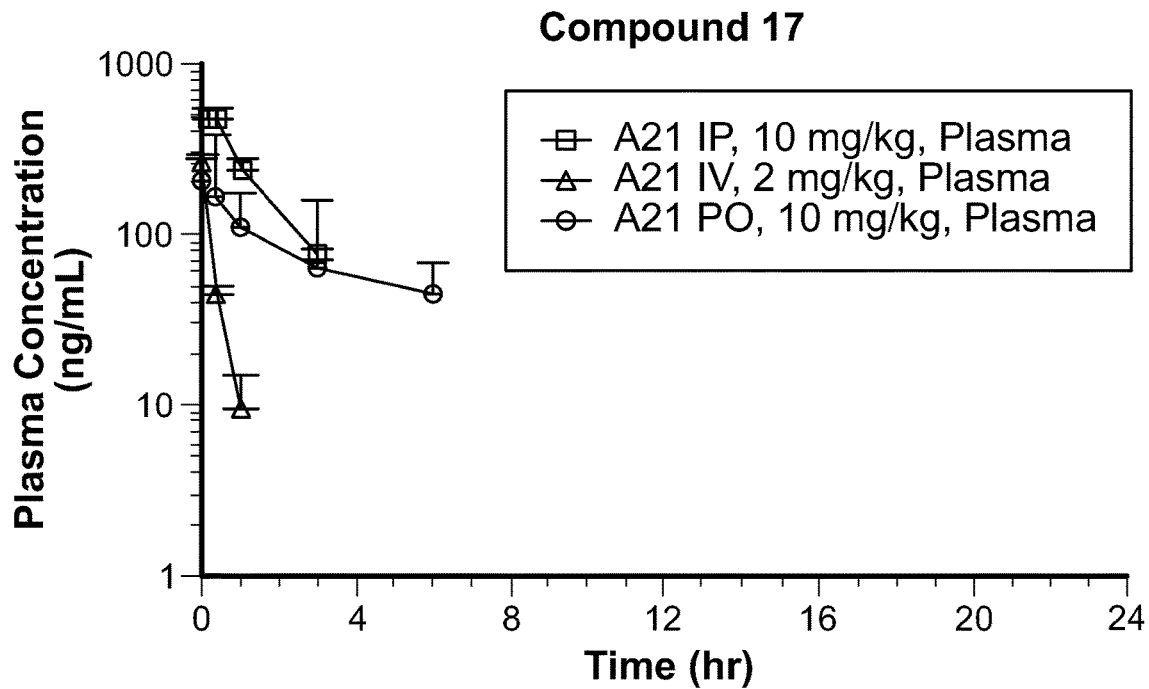
Figure 16:
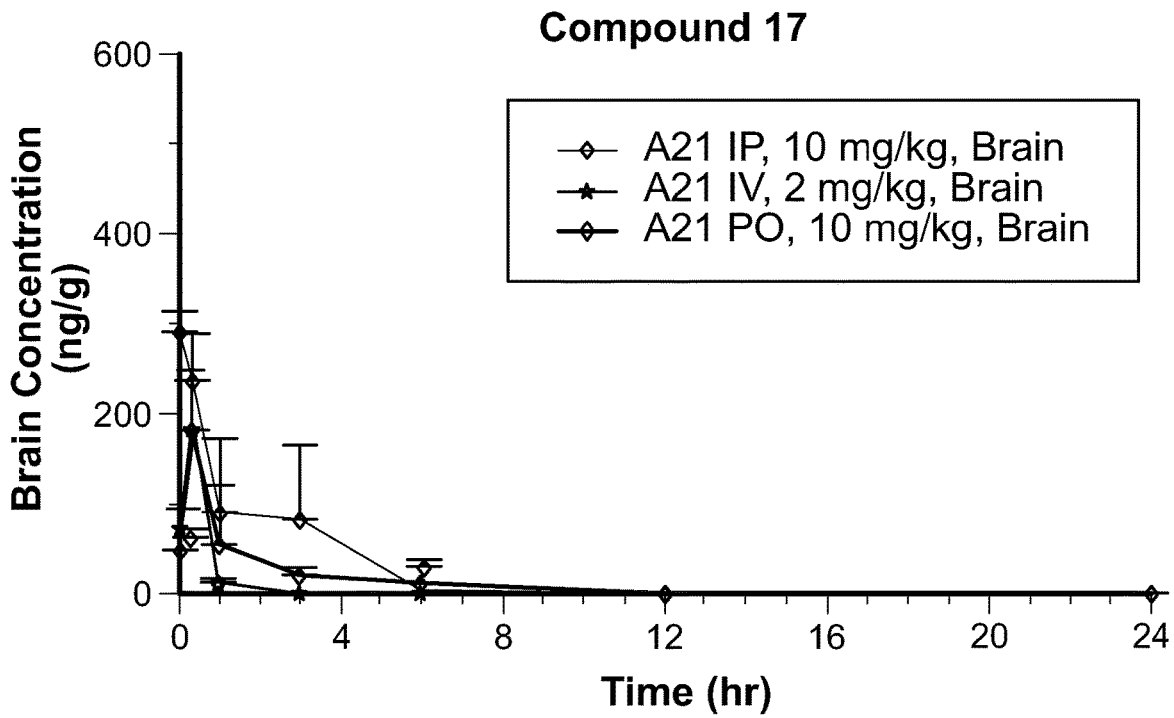
FIG. 16. Shows mean brain concentration-time profiles of Compound 17 following a single intravenous (Dose: 2 mg/kg), intraperitoneal (Dose: 10 mg/kg) and oral (Dose: 10 mg/kg) administration in male C57BL/6 mice from Example 14.
Figure 16:
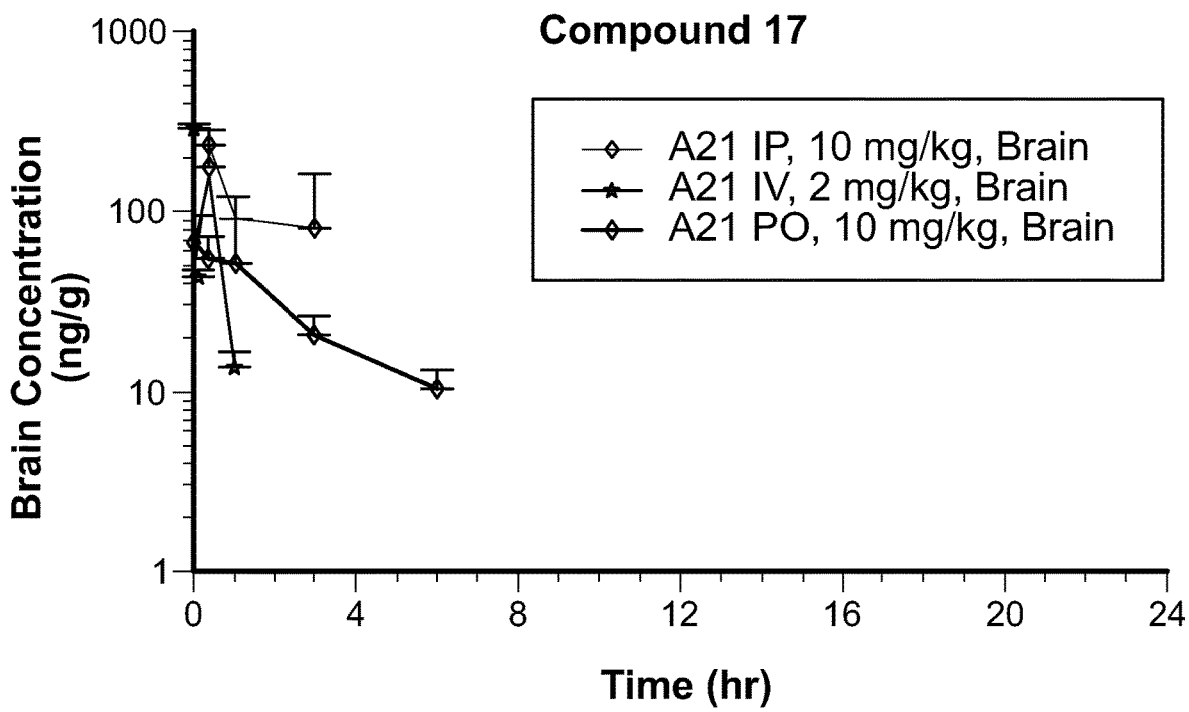

Data for Compound 17 is provided in Tables 24-32 and in FIGS. 15-16.

TABLE 24

Summary of mean plasma and brain pharmacokinetic parameters of Compound 17 following a single intravenous (2 mg/kg), intraperitoneal (10 mg/kg) and oral (10 mg/kg) dose administration in male C57BL/6

| Matrix | Route | Dose (mg/kg) | $T_{max}$ (hr) | $^aC_o/C_{max}$ (ng/mL) | $AUC_{last}$ (hr*ng/mL) | $AUC_{inf}$ (hr*ng/mL) | $T_{1/2}$ (hr) | CL (mL/min/kg) | $V_{ss}$ (L/kg) | % $F^b$ |
|---|---|---|---|---|---|---|---|---|---|---|
| Plasma | IV | 2 | — | 429.68 | 85.73 | 88.20 | 0.21 | NR (377.95) | 4.40 | — |
|  | IP | 10 | 0.08 | 469.08 | 675.48 | 785.70 | — | — | — | — |
|  | PO | 10 | 0.08 | 206.94 | 482.17 | NR | — | — | — | ~100 (112) |

| Matrix | Route | Dose (mg/kg) | $T_{max}$ (hr) | $^aC_o/C_{max}$ (ng/g) | $AUC_{last}$ (hr*ng/g) | $AUC_{inf}$ (hr*ng/g) | $T_{1/2}$ (hr) | CL (mL/min/kg) | $V_{ss}$ (L/kg) | % $F^b$ |
|---|---|---|---|---|---|---|---|---|---|---|
| Brain | IV | 2 | — | 44.87 | 97.08 | NC | NC | NC | NC | — |
|  | IP | 10 | 0.08 | 288.04 | 360.87 | NR | — | — | — | — |
|  | PO | 10 | 0.08 | 67.32 | 171.84 | 204.06 | — | — | — | — |

[a] back extrapolated conc. for i.v. group;
[b] $AUC_{last}$ was considered for calculating oral bioavailability
NC—Not calculated due to insufficient data
NR—Not reportable since AUC_% Extrap_Pred is more than 20%
NR (Clearance): Clearance is not reportable since very high value (377.95 mL/min/kg)

Following a single intravenous dose administration of Compound 17 to male C57BL/6 mice at 2 mg/kg, compound showed high plasma clearance (377.95 mL/min/kg; normal liver blood flow in mice is 90 mL/min/kg) with terminal elimination half-life of 0.21 hours. The Vss was 6.3-fold more than normal volume of total body water (0.7 L/kg). Brain concentrations were quantifiable up to 1 hour and brain-to-plasma ratio ranged 0.18-4.03.

Following a single intraperitoneal dose administration of Compound 17 to male C57BL/6 mice at 10 mg/kg, plasma concentrations were quantifiable up to 6 hours with $T_{max}$ of 0.08 hour. Brain concentrations were quantifiable up to 6 hour and brain-to-plasma ratio ranged 0.39-1.10.

Following a single oral dose administration of Compound 17 to male C57BL/6 mice at 10 mg/kg, plasma concentrations were quantifiable up to 6 hour with $T_{max}$ of 0.08 hour. Brain concentrations were quantifiable up to 6 hour and brain-to-plasma ratio ranged 0.23-0.48. Oral bioavailability of Compound 17 was >100% (112%).

Table 25 (FIG. 19) shows the mean plasma and brain pharmacokinetic parameters of Compound 17 following a single intravenous (Dose: 2 mg/kg), intraperitoneal (Dose: 10 mg/kg) and oral (Dose: 10 mg/kg) dose administration in male C57BL/6 mice.

TABLE 26

Mean brain-to-plasma concentration ratio of Compound 17 following a single intravenous (Dose: 2 mg/kg), intraperitoneal (Dose: 10 mg/kg) and oral (Dose: 10 mg/kg) dose administration in male C57BL/6 mice.

| Route | Dose (mg/kg) | Time (hr) | Plasma Conc. (ng/mL) | [#]Brain Conc. (ng/g) | Brain-to-plasma ratio |
|---|---|---|---|---|---|
| IV | 2 | 0.08 | 256.23 | 44.87 | 0.18 |
|  |  | 0.35 | 44.76 | 180.31 | 4.03 |
|  |  | 1 | 9.57 | 13.83 | 1.45 |
|  |  | 3 | 0.00 | 0.00 | NA |
|  |  | 6 | 0.00 | 0.00 | NA |
|  |  | 12 | 0.00 | 0.00 | NA |
|  |  | 24 | 0.00 | 0.00 | NA |
| IP | 10 | 0.08 | 469.08 | 288.04 | 0.61 |
|  |  | 0.35 | 457.83 | 236.37 | 0.52 |
|  |  | 1 | 232.40 | 90.35 | 0.39 |
|  |  | 3 | 74.86 | 82.02[d] | 1.10 |
|  |  | 6 | 43.71[c] | 25.98[c] | 0.59 |
|  |  | 12 | 0.00 | 0.00 | NA |
|  |  | 24 | 0.00 | 0.00 | NA |
| PO | 10 | 0.08 | 206.94 | 67.32 | 0.33 |
|  |  | 0.35 | 163.27 | 52.98 | 0.32 |
|  |  | 1 | 108.67[d] | 51.91 | 0.48 |
|  |  | 3 | 63.45 | 20.47 | 0.32 |
|  |  | 6 | 45.49 | 10.49[d] | 0.23 |
|  |  | 12 | 0.00 | 0.00 | NA |
|  |  | 24 | 0.00 | 0.00 | NA |

[#]Brain conc. as ng/g, density of brain tissue was considered as 1 which is equivalent to plasma density (1);
NA—Not applicable;
[d] Average of two values considered for analysis;
[c] Single value considered for analysis

TABLE 27

Individual plasma concentration-time data of Compound 17 following a single intravenous administration in male C57BL/6 mice (Dose: 2 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 1 | 238.74 | | | | | | |
| 2 | 259.88 | | | | | | |
| 3 | 270.07 | | | | | | |
| 4 | | 41.48 | | | | | |
| 5 | | 43.10 | | | | | |
| 6 | | 49.70 | | | | | |
| 7 | | | 14.31 | | | | |
| 8 | | | 4.06 | | | | |
| 9 | | | 10.33 | | | | |
| 10 | | | | 0.00 | | | |
| 11 | | | | 0.00 | | | |
| 12 | | | | 0.00 | | | |
| 13 | | | | | 0.00 | | |
| 14 | | | | | 0.00 | | |
| 15 | | | | | 0.00 | | |
| 16 | | | | | | 0.00 | |
| 17 | | | | | | 0.00 | |
| 18 | | | | | | 0.00 | |
| 19 | | | | | | | 0.00 |
| 20 | | | | | | | 0.00 |
| 21 | | | | | | | 0.00 |
| Mean | 256.23 | 44.76 | 9.57 | 0.00 | 0.00 | 0.00 | 0.00 |
| SD | 15.98 | 4.35 | 5.17 | 0.00 | 0.00 | 0.00 | 0.00 |
| CV % | 6.2 | 9.7 | 54.0 | NA | NA | NA | NA |

LLOQ = 2.01 ng/mL;
NA = Not applicable;
No-peaks or values below LLOQ were considered zero

TABLE 28

Individual plasma concentration-time data of Compound 17 following a single intraperitoneal administration in male C57BL/6 mice (Dose: 10 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 22 | 415.53 | | | | | | |
| 23 | 530.31 | | | | | | |
| 24 | 461.39 | | | | | | |
| 25 | | 477.82 | | | | | |
| 26 | | 449.94 | | | | | |
| 27 | | 445.74 | | | | | |
| 28 | | | 223.45 | | | | |
| 29 | | | 276.12 | | | | |
| 30 | | | 197.62 | | | | |
| 31 | | | | 15.93 | | | |
| 32 | | | | 166.82 | | | |
| 33 | | | | 41.84 | | | |
| 34 | | | | | 0.00 | | |
| 35 | | | | | 0.00 | | |
| 36 | | | | | 43.71 | | |
| 37 | | | | | | 0.00 | |
| 38 | | | | | | 0.00 | |
| 39 | | | | | | 0.00 | |
| 40 | | | | | | | 0.00 |
| 41 | | | | | | | 0.00 |
| 42 | | | | | | | 0.00 |
| Mean | 469.08 | 457.83 | 232.40 | 74.86 | 43.71[c] | 0.00 | 0.00 |
| SD | 57.77 | 17.44 | 40.01 | 80.68 | NA | 0.00 | 0.00 |
| CV % | 12.3 | 3.8 | 17.2 | 107.8 | NA | NA | NA |

LLOQ = 2.01 ng/mL;
NA = Not applicable;
No-peaks or values below LLOQ were considered zero
[c]Value excluded from data analysis

TABLE 29

Individual plasma concentration-time data of Compound 17 following a single oral administration in male C57BL/6 mice (Dose: 10 mg/kg)

| Animal ID | Plasma concentration (ng/mL) Time (hr) | | | | | | |
|---|---|---|---|---|---|---|---|
| | 0.08 | 0.35 | 1 | 3 | 6 | 12 | 24 |
| 43 | 255.34 | | | | | | |
| 44 | 127.22 | | | | | | |
| 45 | 238.26 | | | | | | |
| 46 | | 46.88 | | | | | |
| 47 | | 403.86 | | | | | |
| 48 | | 39.07 | | | | | |
| 49 | | | 154.92 | | | | |
| 50 | | | 0.00 | | | | |
| 51 | | | 62.41 | | | | |
| 52 | | | | 62.61 | | | |
| 53 | | | | 69.06 | | | |
| 54 | | | | 58.69 | | | |
| 55 | | | | | 68.70 | | |
| 56 | | | | | 43.09 | | |
| 57 | | | | | 24.69 | | |
| 58 | | | | | | 0.00 | |
| 59 | | | | | | 0.00 | |
| 60 | | | | | | 0.00 | |
| 61 | | | | | | | 0.00 |
| 62 | | | | | | | 0.00 |
| 63 | | | | | | | 0.00 |
| Mean | 206.94 | 163.27 | 108.67[d] | 63.45 | 45.49 | 0.00 | 0.00 |
| SD | 69.57 | 208.39 | NA | 5.24 | 22.10 | 0.00 | 0.00 |
| CV % | 33.6 | 127.6 | NA | 8.3 | 48.6 | NA | NA |

LLOQ = 2.01 ng/mL;
NA = Not applicable;
No-peaks or values below LLOQ were considered zero
[d]Average of two values considered for data analysis

TABLE 30

Individual brain (ng/g) concentration-time data of Compound 17 following a single intravenous administration in male C57BL/6 mice (Dose: 2 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| 1 | 45.69 | | | | | | |
| 2 | 44.67 | | | | | | |
| 3 | 44.25 | | | | | | |
| 4 | | 163.35 | | | | | |
| 5 | | 121.17 | | | | | |
| 6 | | 256.41 | | | | | |
| 7 | | | 17.13 | | | | |
| 8 | | | 11.76 | | | | |
| 9 | | | 12.60 | | | | |
| 10 | | | | 0.00 | | | |
| 11 | | | | 0.00 | | | |
| 12 | | | | 0.00 | | | |
| 13 | | | | | 0.00 | | |
| 14 | | | | | 0.00 | | |
| 15 | | | | | 0.00 | | |
| 16 | | | | | | 0.00 | |
| 17 | | | | | | 0.00 | |
| 18 | | | | | | 0.00 | |
| 19 | | | | | | | 0.00 |
| 20 | | | | | | | 0.00 |
| 21 | | | | | | | 0.00 |
| Mean | 44.87 | 180.31 | 13.83 | 0.00 | 0.00 | 0.00 | 0.00 |
| SD | 0.74 | 69.20 | 2.89 | 0.00 | 0.00 | 0.00 | 0.00 |
| CV % | 1.7 | 38.4 | 20.9 | NA | NA | NA | NA |

LLOQ = 3.00 ng/g,
NA—Not applicable;
No peaks or values below LLOQ were considered zero
Brain conc. as ng/g, density of brain tissue was considered as 1 which is equivalent to plasma density (1)

TABLE 31

Individual brain (ng/g) concentration-time data of Compound 17 following a single intraperitoneal administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| 22 | 314.55 | | | | | | |
| 23 | 285.45 | | | | | | |
| 24 | 264.12 | | | | | | |
| 25 | | 290.76 | | | | | |
| 26 | | 183.93 | | | | | |
| 27 | | 234.42 | | | | | |
| 28 | | | 65.91 | | | | |
| 29 | | | 124.80 | | | | |
| 30 | | | 80.34 | | | | |
| 31 | | | | 5.16$^e$ | | | |
| 32 | | | | 139.86 | | | |
| 33 | | | | 24.18 | | | |
| 34 | | | | | 25.98 | | |
| 35 | | | | | 0.00 | | |
| 36 | | | | | 0.00 | | |
| 37 | | | | | | 0.00 | |
| 38 | | | | | | 0.00 | |
| 39 | | | | | | 0.00 | |
| 40 | | | | | | | 0.00 |
| 41 | | | | | | | 0.00 |
| 42 | | | | | | | 0.00 |
| Mean | 288.04 | 236.37 | 90.35 | 82.02$^d$ | 25.98$^e$ | 0.00 | 0.00 |
| SD | 25.31 | 53.44 | 30.69 | NA | NA | 0.00 | 0.00 |
| CV % | 8.8 | 22.6 | 34.0 | NA | NA | NA | NA |

LLOQ = 3.00 ng/g,
NA—Not applicable;
No peaks or values below LLOQ were considered zero
Brain conc. as ng/g, density of brain tissue was considered as 1 which is equivalent to plasma density (1),
$^c$Value excluded from data analysis
$^d$Average of two values considered for data analysis
$^e$Value excluded from data analysis

TABLE 32

Individual brain (ng/g) concentration-time data of Compound 17 following a single oral administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| 43 | 93.03 | | | | | | |
| 44 | 40.65 | | | | | | |
| 45 | 68.28 | | | | | | |
| 46 | | 43.59 | | | | | |
| 47 | | 39.90 | | | | | |
| 48 | | 75.45 | | | | | |
| 49 | | | 91.08 | | | | |
| 50 | | | 13.08 | | | | |
| 51 | | | 51.57 | | | | |
| 52 | | | | 28.05 | | | |
| 53 | | | | 17.64 | | | |
| 54 | | | | 15.72 | | | |
| 55 | | | | | 8.79 | | |
| 56 | | | | | 0.00 | | |
| 57 | | | | | 12.18 | | |
| 58 | | | | | | 0.00 | |
| 59 | | | | | | 0.00 | |
| 60 | | | | | | 0.00 | |
| 61 | | | | | | | 0.00 |
| 62 | | | | | | | 0.00 |
| 63 | | | | | | | 0.00 |

TABLE 32-continued

Individual brain (ng/g) concentration-time data of Compound 17 following a single oral administration in male C57BL/6 mice (Dose: 10 mg/kg)

| Animal ID | #Brain concentration (ng/g) Time (hr) | | | | | | |
|---|---|---|---|---|---|---|---|
| | 0.08 | 0.35 | 1 | 3 | 6 | 12 | 24 |
| Mean | 67.32 | 52.98 | 51.91 | 20.47 | 10.49$^d$ | 0.00 | 0.00 |
| SD | 26.20 | 19.55 | 39.00 | 6.63 | NA | 0.00 | 0.00 |
| CV % | 38.9 | 36.9 | 75.1 | 32.4 | NA | NA | NA |

LLOQ = 3.00 ng/g,
NA—Not applicable;
$^d$Average of two values considered for data analysis
Brain conc. as ng/g, density of brain tissue was considered as 1 which is equivalent to plasma density (1),
No peaks or values below LLOQ were considered zero Summary Data A summary oft comparative biological data for Compounds 100, 101, 14, 15, 16, and 17 is provided in Table 33 (FIG. 20). The biological activity for certain compounds is also summarized below.

Compound 100
  Potency in patient derived GBM spheres: 5 nM.
  Potency in GBM cells: 5 nM.
  Caco permeability: Moderately high.
  PPB: Mod/High.
  Metabolic stability in liver microsomes: (stable in -NAPDH and buffer samples): at 60 min: 26%, at 60 min (-NAPDH or Buffer): 90%.
  Pharmacokinetics and brain to plasma levels: T max (hr): 0.25
  Oral bioavailability: 4%.
Compound 101
  Potency in patient derived GBM spheres: 50 nM.
  Potency in GBM cells: 10 nM.
  Other features and in vivo assays: not done (ND).
Compound 14
  Potency in patient derived GBM spheres: 10 nM.
  Cellular assays: Lowered BMI1 levels, lowered STAT1, and lowered pRB.
  Caco permeability: No/low permeability.
  PPB at 4 h: 76%.
  Metabolic stability in liver microsomes: <50%.
  Brain to plasma levels: ND.
  Oral bioavailability: ND
Compound 15
  Potency in patient derived GBM spheres: 1 uM.
  Cellular assays: slightly lowered BMI1 levels, lowered STAT1, and lowered pRB.
  Caco permeability: No/low permeability.
  PPB at 4 h: 90%.
  Metabolic stability in liver microsomes: <50%.
  Brain to plasma ratio following a single oral dose: 1.03.
  Oral bioavailability: 64%
Compound 16
  Potency in patient derived GBM spheres: 10 nM.
  Caco permeability: Moderate and not P-gp substrate with efflux ratio 0.9.
  PPB at 4 h: 76%.
  Metabolic stability in liver microsomes: <50%.
  Brain to plasma ratio following a single oral dose: 1.81.
  Oral bioavailability: 20%

Compound 17

Potency in patient derived GBM spheres: 10 nM.

Cellular assays: Lowered BMI1 levels, lowered STAT1, lowered pRB, and increased PDL1 (possible immune checkpoint modulating activity).

Caco permeability: Moderate and not P-gp substrate with efflux ratio 1.3.

PPB at 4 h: 75%.

Metabolic stability in liver microsomes: <50%.

Brain to plasma ratio following a single oral dose: 0.48.

Oral bioavailability: >100% (112%).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound, which is:

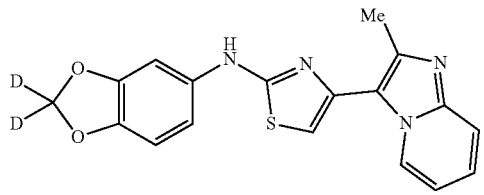 [SMILES: [2H]C1([2H])Oc2ccc(Nc3nc(-c4c(C)nc5ccccn45)cs3)cc2O1]

or salt thereof.

2. A pharmaceutical composition, comprising, the compound of claim 1 or a pharmaceutically acceptable salt thereof, and a pharmaceutically acceptable carrier.

3. A method for treating glioblastoma in an animal comprising administering to the animal an effective amount of the compound of claim 1 or a pharmaceutically acceptable salt thereof.

* * * * *